(12) United States Patent
Kermekchiev et al.

(10) Patent No.: US 9,796,965 B2
(45) Date of Patent: Oct. 24, 2017

(54) USE OF TAQ POLYMERASE MUTANT ENZYMES FOR NUCLEIC ACID AMPLIFICATION IN THE PRESENCE OF PCR INHIBITORS

(71) Applicant: DNA Polymerase Technology Inc., St. Louis, MO (US)

(72) Inventors: Milko Kermekchiev, St. Louis, MO (US); Lyubka Kirilova, Maryland Heights, MO (US); Zhian Zhang, Ballwin, MO (US)

(73) Assignee: DNA Polymerase Technology, Inc., St. Louis, MO (US)

( * ) Notice: Subject to any disclaimer, the term of this patent is extended or adjusted under 35 U.S.C. 154(b) by 0 days.

(21) Appl. No.: 14/746,982

(22) Filed: Jun. 23, 2015

(65) Prior Publication Data

US 2015/0368624 A1 Dec. 24, 2015

Related U.S. Application Data

(60) Division of application No. 12/441,521, filed on Mar. 16, 2009, now abandoned, which is a continuation-in-part of application No. PCT/US2007/078571, filed on Sep. 14, 2007.

(60) Provisional application No. 60/825,692, filed on Sep. 14, 2006.

(51) Int. Cl.
*C12N 9/12* (2006.01)
*C12Q 1/68* (2006.01)

(52) U.S. Cl.
CPC ........... *C12N 9/1241* (2013.01); *C12Q 1/686* (2013.01)

(58) Field of Classification Search
None
See application file for complete search history.

(56) References Cited

U.S. PATENT DOCUMENTS

| | | |
|---|---|---|
| 5,436,149 A | 7/1995 | Barnes |
| 5,501,963 A | 3/1996 | Burckhardt |
| 5,616,494 A | 4/1997 | Barnes |
| 6,818,431 B1 | 11/2004 | Hong et al. |
| 2004/0005594 A1 | 1/2004 | Holliger et al. |
| 2004/0161767 A1 | 8/2004 | Baldwin et al. |
| 2005/0250131 A1 | 11/2005 | Jestin et al. |
| 2005/0260606 A1 | 11/2005 | Kermekchiev et al. |
| 2006/0084074 A1 | 4/2006 | Kermekchiev et al. |
| 2007/0048748 A1 | 3/2007 | Williams et al. |
| 2007/0111234 A1 | 5/2007 | Birkner et al. |
| 2008/0014609 A1 | 1/2008 | Jestin et al. |
| 2008/0166772 A1 | 7/2008 | Hollinger et al. |
| 2009/0170060 A1 | 7/2009 | Kermekchiev et al. |

FOREIGN PATENT DOCUMENTS

| | | |
|---|---|---|
| WO | WO 2004/013279 | 2/2004 |
| WO | WO 2005/113829 | 12/2005 |

OTHER PUBLICATIONS

Kermeckchiev et al., Nuceic Acids Research vol. 37, No. 5, p. e40, Feb. 2009.*
Akane et al., Identification of heme compound copurified with deoxyribonucleic acid (DNA) from bloodstains, a major inhibitor of polymerase chain reaction (PCR) amplification, Journal of Forensic Science, 1994, pp. 362-372, vol. 39.
Al-Soud et al., A sample preparation method which facilitates detection of bacteria in blood cultures by the polymerase chain reaction, Journal of Microbiological Methods, 1998, pp. 217-224, vol. 32.
Al-Soud et al., Capacity of nine thermostable DNA polymerases to mediate DNA amplification in the presence of PCR-inhibiting samples, Applied and Environmental Microbiology, 1998, pp. 3748-3753, vol. 64, No. 10.
Al-Soud et al., Effects of amplification facilitators in diagnostic PCR in the presence of blood, feces and meat, Journal of Clinical Microbiology, 2000, pp. 4463-4470, vol. 38, No. 12.
Al-Soud et al., Purification and characterization of PCR-Inhibitory components in blood cells, Journal of Clinical Microbiology, 2001, pp. 485-493, vol. 39.
Al-Soud et al., Identification and characterization of immunoglobulin G in blood as a major inhibitor of diagnostic PCR, Journal of Clinical Microbiology, 2000, pp. 345-350, vol. 38, No. 1.
Altwegg et al., Amplification methods in diagnostic microbiology, Journal of Microbiological Methods, 1995, pp. 3-138, vol. 23.
Australian Office Action dated May 8, 2012 in related Application No. 2007296180, 4 Pages.
Barnes, The fidelity of *Taq* polymerase catalyzing PCR is improved by an N-terminal deletion, Gene, 1992, pp. 29-35, vol. 112.
Barnes, PCR amplification of up to 35kb DNA with high fidelity and high yield from bacteriophage templates, Proc. Natl. Sci. , 1994, USA, pp. 2216-2220, vol. 91.
Barnes, Tips and tricks for long and accurate PCR, TIBS, 1994, pp. 342-346, vol. 19.
Baskaran et al., Uniform amplification of a mixture of deoxyribonucleic acids with varying GC content, Genome Research, 1996, pp. 633-638, vol. 6.
Bourke et al., NaOH treatment to neutralize inhibitors of Taq polymerase, Journal of Forensic Sciences, 1999, pp. 1046-1050, vol. 44.
Burckhardt, Amplification of DNA from Whole Blood, PCR Methods Applications, Cold Spring Harbor Laboratory Press, 1994, pp. 239-243, vol. 3, No. 4.

(Continued)

*Primary Examiner* — Richard Hutson
(74) *Attorney, Agent, or Firm* — Senniger Powers LLP

(57) ABSTRACT

The present invention generally relates to detection of a target nucleic acid in standard PCR, real-time PCR, RT PCR, and real-time RT PCR. One aspect of the invention provides mutant DNA polymerase enzymes that are resistant to PCR inhibitors, such as dye, blood, and soil. Another aspect of the invention provides for methods of real-time PCR assays using mutant DNA polymerase enzymes resistant to PCR inhibitors with samples containing dye, blood, and/or soil. Another aspect of the invention provides for methods of standard PCR assays using mutant DNA polymerase enzymes resistant to PCR inhibitors with samples containing blood and/or soil.

20 Claims, 31 Drawing Sheets

(56) References Cited

OTHER PUBLICATIONS

Cattaneo et al., Comparison of three DNA extraction methods on bone and blood stains up to 43 years old and amplification of three different gene sequences, Journal of Forensic Sciences, 1997, pp. 1126-1135, vol. 42.
De Franchis et al., A potent inhibitor of Taq polymerase copurifies with human genomic DNA, 1988, Nucleic Acids, Res., pp. 10355, vol. 16.
European Office Action dated Nov. 22, 2013 in related European Application No. 07842556.8, filed Sep. 14, 2007, 9 pages.
Frackman et al., Betaine and DMSO: enhancing agents for PCR, Promega Notes, 1998, pp. 27-30, vol. 65.
GenBank Accession No. J04639, NCBI webpage last accessed Aug. 28, 2009, 3 pages.
Ghadessy et al., Directed evolution of polymerase function by compartmentalized self-replication, Proc. Natl. Acad. Sci. USA, 2001, pp. 4552-4557, vol. 98, No. 8.
Gundry et al., Amplicon melting analysis with labeled primers: a closed-tube method for differentiating homozygotes and heterozygotes, Clinical Chemistry, 2003, pp. 396-406, vol. 49, No. 3.
International Search Report dated Oct. 7, 2008, in the related application PCT/US2007/078571, 1 page.
Izraeli et al., Detection of gene expression by PCR amplification of RNA derived from frozen heparinized whole blood, Nucleic Acids Research, 1991, pp. 6051, vol. 19, No. 21.
Japanese Official Action dated Nov. 6, 2012 in related Japanese Application No. 2009-528518, in English and Japanese, 7 pages.
Kellogg et al., TaqStart Antibody: "hot start" PCR facilitated by a neutralizing monoclonal antibody directed against *Taq* DNA polymerase, BioTechniques, 1994, pp. 1134-1137, vol. 16, No. 6.
Kermekchiev et al., Cold-Sensitive Mutants of Taq DNA Polymerase a Hot Start for PCR, Nucleic Acids Research, 2003, pp. 6139-6147, vol. 31, No. 21.
Klein et al., Comparison of methods for extraction of nucleic acid from hemolytic serum for PCR amplification of hepatitis B virus DNA sequences, Journal of Clinical Microbiology, 1997, pp. 1897-1899, vol. 35, No. 7.
Kox et al., A more reliable PCR for detection of *Mycobacterium tuberculosis* in clinical samples, Journal of Clinical Microbiology, 1994, pp. 672-680, vol. 32, No. 3.
Kramvis et al., Comparison of hepatitis B virus DNA extractions from serum by the QIAmp blood kit, GeneReleaser and the phenol-chloroform method, Journal of Clinical Microbiology, 1996, pp. 2731-2733, vol. 34, No. 11.
Lamontagne et al., Evaluation of extraction and purification methods for obtaining PCR-amplifiable DNA from compost for microbial community analysis, Journal of Microbiological Methods, 2002, pp. 255-264, vol. 49.
Lantz et al., Biotechnical use of the polymerase chain reaction for microbial analysis of biological samples, Biotechnology Annual Review, 2000, pp. 87-130, vol. 5.
Lawyer et al., Isolation, Characterization, and Expression in *Escherichia coli* of the DNA polymerase gene from *Thermus aquaticus*, The Journal of Biological Chemistry, 1989, pp. 6427-6437, vol. 254, No. 11.
Link et al., Beyond toothpicks: new methods for isolating mutant bacteria, Nature Reviews, 2007, pp. 680-688, vol. 5, No. 9.
Monis et al., Comparison of SYTO9 and SYBR Green I for real-time polymerase chain reaction and investigation of the effect of dye concentration on amplification and DNA melting curve analysis, Analytical Biochemistry, 2005, pp. 24-34, vol. 340.
Morata et al., Strategy for optimizing DNA amplification in a peripheral blood PCR assay used for diagnosis of human brucellosis, Journal of Clinical Microbiology, 1998, pp. 2443-2446, vol. 36, No. 9.
Nath et al., Effects of ethidium bromide and SYBR Green I on different polymerase chain reaction systems, Journal of Biochemical and Biophysical Methods, 2000, pp. 15-29, vol. 42.
Ngo et al., Computational complexity, protein structure prediction, and the levinthal paradox, The Protein Folding Problem and Tertiary Structure Prediction, 1994, pp. 491-495.
Panaccio et al., PCR based diagnosis in the presence of 8% (viv) Blood, Nucleic Acids Research, 1991, pp. 1151, vol. 19, No. 5.
Rossen et al., Inhibition of PCR by components of food samples, microbial diagnostic assays and DNA-extraction solution, International Journal of Food Microbiology, 1992, pp. 37-45, vol. 17.
Sanger et al., Rapid filter assay for the detection of DNA polymerase activity: direct identification of the gene for the DNA polymerase from *Thermus aquaticus*, Gene, 1991, pp. 119-123, vol. 97, No. 1.
Scalice et al., Monoclonal antibodies prepared against the DNA polymerase from *Thermus aquaticus* are potent inhibitors of enzyme activity, Journal of Immunological Methods, 1994, pp. 147-163, vol. 172.
Sharkey et al., Antibodies as thermolabile switches: high temperature triggering for the polymerase chain reaction, Biotechnology, 1994, pp. 506-509, vol. 12.
Stubner, Enumeration of 16S rDNA of *Desulfotomaculum* lineage 1 in rice field soil by real-time PCR with SybrGreen™ detection, Journal of Microbiological Methods, 2002, pp. 155-164, vol. 50.
Supplemental European Search Report dated Apr. 9, 2010, in related application No. EP 07 84 2556.
Tabor et al., A single residue in DNA polymerases of the *Escherichia coli* DNA polymerase I family is critical for distinguishing between deoxy- and dideoxyribonucleotides, Proc. Natl. Acad. Sci. USA, 1995, pp. 6339-6343, vol. 92.
Tawfik et al., Man-made cell-like compartments for molecular evolution, Nature Biotechnology, 1998, pp. 652-656.
Topal et al., Products of bacteriophage T5 genes 32 and 45 improve the accuracy of DNA replication in Vitro, The Journal of Biological Chemistry, 1983, pp. 12274-12279, vol. 258, No. 20.
Tsai et al., Rapid method for separation of bacterial DNA from humic substances in sediments for polymerase chain reaction, Applied and Environmental Microbiology, 1992, pp. 2292-2295, vol. 58, No. 7.
Watson et al., Purification and characterization of a common soil component which inhibits the polymerase chain reaction, Can. J. Microbiol., 2000, pp. 633-642, vol. 46.
Wilson, Inhibition and facilitation of nucleic acid amplification, Applied and Environmental Microbiology, 1997, pp. 3741-3751, vol. 63, No. 10.
Yeates et al., Methods for microbial DNA extraction from soil for PCR amplification, Biological Procedures Online, 1998, pp. 40-47, vol. 1, No. 1.
Zhong et al., Sensitive and specific detection of carcinoembryonic antigen cDNA using the hot start polymerase chain reaction technique, Clinical Laboratory Publications, 2000, pp. 7-11, vol. 46.
Steitz, Thomas A., "DNA Polymerases: Structural Diversity and Common Mechanisms," The Journal of Biological Chemistry, Issue of Jun. 18, 1999, vol. 274, No. 25, pp. 17395-17398.
Higuchi et al., "Kinetic PCR Analysis: Real-time Monitoring of DNA Amplification Reactions," Biotechnology, Sep. 1993, vol. 11(9), pp. 1026-1030.

* cited by examiner wt KlenTaq

KlenTaq 10

FLAC-22

Fast Start wt KlenTaq (10% blood)

wt KlenTaq (5% blood)

KlenTaq-10 (10% blood)

KlenTaq-10 (5% blood)

FLAC-22

Fast Start

FLAC-22

KlenTaq-10

Fast Start

Jump Start

AmpliTaq Gold

USE OF TAQ POLYMERASE MUTANT ENZYMES FOR NUCLEIC ACID AMPLIFICATION IN THE PRESENCE OF PCR INHIBITORS

CROSS-REFERENCE TO RELATED APPLICATIONS

This application is a Divisional application of U.S. Non-Provisional application Ser. No. 12/441,521, filed 16 Mar. 2009, which claims priority from Continuation-in-Part of PCT/US07/78571, filed 14 Sep. 2007, which claims priority from U.S. Provisional Application Ser. No. 60/825,692 filed on 14 Sep. 2006, each of which is incorporated herein by reference in its entirety.

STATEMENT REGARDING FEDERALLY SPONSORED RESEARCH OR DEVELOPMENT

This invention was made with Government support under Grant No. 2R44GM073401 awarded by National Institute of Health. The government has certain rights in the invention.

INCORPORATION-BY-REFERENCE OF MATERIAL SUBMITTED ON A COMPACT DISC

The Sequence Listing, which is a part of the present disclosure, includes a computer readable form, filed electronically via EFS-Web, comprising nucleotide and/or amino acid sequences of the present invention. The subject matter of the Sequence Listing is incorporated herein by reference in its entirety.

FIELD OF THE INVENTION

The present invention generally relates to nucleic acid detection in standard and real-time PCR and RT PCR.

BACKGROUND

Standard and real time polymerase chain reaction (PCR) assays are limited by inhibitors found in many common sample types as well as components of the PCR assays themselves. Examples of PCR inhibitors include those found in commercial dyes used in PCR as well as those found in blood and soil.

Commonly used fluorescent dyes, such as SYBR Green, can significantly inhibit the Taq polymerase (GenBank Accession No. J04639; SEQ ID NO: 4) at concentrations higher than about 0.25-1×. This dye inhibition of Taq polymerase imposes limitations on the sensitivity and product specificity and may cause dye-dependant false negative results (see e.g., Monis et al. (2005) Anal Biochem 340, 24-34; Stubner (2002) J Microbiol Methods 50, 155-64; Nath et al. (2000) J Biochem Biophys Methods 42, 15-29; Gundry et al. (2003) Clin. Chem. 2003; 49:396-406).

The success and sensitivity of DNA detection in important clinical, diagnostic and forensic applications of PCR of blood specimens is limited by the presence of blood inhibitors of Taq polymerase, such as the heme, IgG fractions, and other blood components. Plain Taq enzyme can be completely inhibited between 0.004% and 0.2% blood (vol/vol) (see e.g., Al-Soud et al. (2000) J. Clin. Microbiol. 38, 4463-70; Al-Soud et al. (2000) J. Clin. Microbiol. 38, 345-50; Al-Soud et al. (1998) Environ. Microbiol. 64, 3748-53). In order to overcome this inhibition, high cost and additional labor-demanding methods are currently used to purify DNA from blood prior to PCR. Nevertheless, this inhibition is still a serious concern with many PCR-based human blood tests, since even after purifying DNA from the blood, traces of the PCR inhibitors can generate as high as 14% false negative results, as published for hepatitis B blood tests (Kramvis et al. (1996) J Clin Microbiology 34, 2731-2733).

Sensitive and precise PCR detection of microorganisms in soil is necessary, for example, in specific agricultural purposes, infectious disease control, and bioterrorism related pathogen tests. Direct extraction of total DNA from soil samples results in a co-extraction of humic acid, known as the most potent soil inhibitor to PCR analysis. Humic substances represent a mixture of partially characterized polyphenols that are produced during the decomposition of organic matter. Other inhibitory components include fulvic acid, polysaccharides and metal ions that can be present in varying concentrations in the soil samples (see e.g., Tsai et al. (1992) Environ. Microbiol. 58, 2292-2295; Watson et al (2000) Can. J. Microbiol. 46, 633-642; Yeates et al. (1998) Biol. Proced. Online 1, 40-47; LaMontagne et al. (2001) Journal of Microbiological Methods 49, 255-264).

A general technical problem with the soil samples is the high variation in the concentrations of various inhibitory substances, depending on the soil source, which may generate inconsistent results. This fact significantly complicates the development of standard DNA purification protocol for processing the samples before PCR. Unlike blood, crude soil extracts exhibit relatively little or no fluorescence quenching effect in real-time PCR.

U.S. patent application Ser. No. 11/005,559 (incorporated herein by reference in its entirety) describes blood-resistant mutants of Taq DNA polymerase, which can be used to amplify the DNA target directly in blood in standard, non-real-time PCR. Unlike existing protocols, this method requires no DNA purification steps prior to PCR, thus reducing the time and cost of important clinical blood tests. Today's PCR analyses, especially clinical and forensic analyses, increasingly utilize real-time PCR protocols, which allow accurate quantitation of the data. The blood, however, has a strong quenching effect on the fluorescence detected in real-time PCR, and such problem has previously been solved by using higher fluorescent dye concentrations.

Thus, there exists a need for inhibitor-resistant DNA polymerases and methods of their use for gene detection in standard and real-time PCR, both in the presence and absence of blood and soil in the samples, and for real-time assays, the presence of dye.

SUMMARY

Disclosed herein are simple methods for real-time PCR analyses of samples utilizing mutant polymerase enzymes that are dye-resistant; dye- and blood-resistant; dye- and soil-resistant; and or dye-, blood- and soil-resistant.

One aspect provides a method of amplifying a target nucleic acid in a real-time polymerase chain reaction (PCR). The method can include forming an assay mixture comprising a sample, where the sample comprises a target nucleic acid; a plurality of primers specific for the target nucleic acid; a buffer suitable for real-time PCR; at least one dye; and at least one polymerase having dye-resistant activity. The method can include amplifying the target nucleic acid in the assay mixture in a real-time PCR.

In some embodiments, the target nucleic acid is a DNA molecule. In some embodiments, the target nucleic acid is an RNA molecule. In some embodiments, the real-time PCR is a real-time reverse transcriptase (RT) PCR. In some embodiments, the target nucleic acid is an RNA and the real-time PCR is a real-time reverse transcriptase (RT) PCR. In some embodiments, the target nucleic acid is an RNA; the real-time PCR is a real-time reverse transcriptase (RT) PCR; and the assay mixture further comprises a reverse-transcriptase In some embodiments, the at least one polymerase is a dye-resistant and blood-resistant polymerase. In some embodiments, the at least one polymerase is a dye-resistant and soil-resistant polymerase. In some embodiments, the at least one polymerase is a dye-resistant, blood-resistant, and soil-resistant polymerase.

In some embodiments, the at least one polymerase has a polypeptide sequence comprising SEQ ID NO: 1. In some embodiments, the at least one polymerase has a polypeptide sequence at least 95% identical to SEQ ID NO: 1 and polymerase activity. In some embodiments, the at least one polymerase has a polypeptide sequence at least 95% identical to SEQ ID NO: 1; comprises at least one amino acid substitution at an amino acid residue position selected from the group consisting of positions 626, 707, and 708; and has polymerase activity.

In some embodiments, the at least one polymerase has a polypeptide sequence comprising SEQ ID NO: 2. In some embodiments, the at least one polymerase has a polypeptide sequence at least 95% identical to SEQ ID NO: 1 and dye-resistant polymerase activity. In some embodiments, the at least one polymerase having a polypeptide sequence at least 95% identical to SEQ ID NO: 2 comprises at least one amino acid substitution at an amino acid residue position selected from the group consisting of 626, 707, and 708.

In some embodiments, the sample further comprises whole blood or a blood component. In some embodiments, the blood component is blood plasma or blood serum. In some embodiments, the whole blood is at least about 1% up to about 25% of a total volume of the PCR assay mixture. In some embodiments, the blood component is at least about 1% up to about 25% of a total volume of the PCR assay mixture.

In some embodiments, the sample further comprises soil or soil extract. In some embodiments, the soil is at least about 1% up to about 50% of a total volume of the PCR assay mixture. In some embodiments, the soil extract is at least about 1% up to about 90% of a total volume of the PCR assay mixture. In some embodiments, the soil comprises a humic acid and the soil is present in the assay mixture at a soil equivalent amount that provides up to about 25 ng of humic acid per 50 uL reaction volume. In some embodiments, the soil extract comprises a humic acid and the soil extract is present in the assay mixture at a soil extract equivalent amount that provides up to about 25 ng of humic acid per 50 uL reaction volume or soil extract In some embodiments, the at least one dye is a fluorescent dye selected from the group consisting of SYBR Green, Ethidium Bromide, PICO, TOTO, YOYO or LC Green. In some embodiments, the at least one dye is SYBR Green. In some embodiments, the dye is present in the PCR assay mixture at least about 0.5× up to about 256×, where X is a manufacturer unit for concentration for use in PCR.

In some embodiments, the assay mixture further comprises a PCR enhancer. In some embodiments, the PCR enhancer comprises betaine.

Another aspect provides an isolated polypeptide having dye-, soil-, or blood-resistant polymerase activity, or a combination thereof. In some embodiments, the isolated polypeptide comprises a polypeptide sequence of SEQ ID NO: 2. In some embodiments, the isolated polypeptide comprises a polypeptide sequence at least 95% identical to SEQ ID NO: 2 and having dye-, soil-, or blood-resistant polymerase activity, or a combination thereof. In some embodiments, the isolated polypeptide comprises a polypeptide sequence at least 95% identical to SEQ ID NO: 2 comprising at least one amino acid substitution at an amino acid residue position selected from the group consisting of 626, 707, and 708, and having dye-, soil-, or blood-resistant polymerase activity, or a combination thereof.

Another aspect provides a method of amplifying a target nucleic acid in a polymerase chain reaction (PCR) comprising forming an assay mixture comprising a sample comprising a target nucleic acid, wherein the sample optionally contains whole blood or a blood component selected from blood plasma or blood serum, or soil or soil extract; primers specific for the target nucleic acid; a buffer; at least one polymerase described above; and amplifying the target nucleic acid in the assay mixture in a PCR.

Other objects and features will be in part apparent and in part pointed out hereinafter.

BRIEF DESCRIPTION OF THE DRAWINGS

Those of skill in the art will understand that the drawings, described below, are for illustrative purposes only. The drawings are not intended to limit the scope of the present teachings in any way.

FIG. 1A is gel electrophoresis analysis. FIG. 1B is melting curve analysis for wild type KlenTaq. FIG. 1C is melting curve analysis for KlenTaq-10. Further details regarding methodology are presented in Example 1.

FIG. 2A is gel electrophoresis analysis. FIG. 2B is melting curve analysis for FLAC-22. FIG. 2C is melting curve analysis for Fast Start. Further details regarding methodology are presented in Example 3.

FIG. 3A is gel electrophoresis analysis. FIG. 3B is melting curve analysis for wild type KlenTaq with 10% blood. FIG. 3C is melting curve analysis for wild type KlenTaq with 5% blood. FIG. 3D is melting curve analysis for KlenTaq-10 with 10% blood. FIG. 3E is melting curve analysis for KlenTaq-10 with 5% blood. Further details regarding methodology are presented in Example 3.

FIG. 4A is gel electrophoresis analysis. FIG. 4B is a melting curve analysis for FLAC-22. FIG. 4C is a melting curve analysis for Fast Start. Further details regarding methodology are presented in Example 4.

FIG. 5A is a gel electrophoresis analysis of FLAC-22 and KlenTaq-10. FIG. 5B is a gel electrophoresis analysis of Fast Start and Jump Start. FIG. 5C is a gel electrophoresis analysis of AmpliTaq Gold. FIG. 5D is a melting curve analysis of FLAC-22. FIG. 5E is a melting curve analysis of KlenTaq-10. FIG. 5F is a melting curve analysis of Fast Start. FIG. 5G is a melting curve analysis of Jump Start. FIG. 5H is a melting curve analysis of AmpliTaq Gold. Further details regarding methodology are presented in Example 5.

FIG. 6A is a quantitation graph showing fluorescence as a function of PCR c One aspect of the invention is the use of inhibition-resistant mutant DNA polymerase enzymes in real-time PCR assays with crude samples containing, for example, blood and dye, soil and dye, or combination of blood and soil plus dye. Generally, the presence of blood components (e.g., heme) in a PCR reaction mixture significantly quenches dye fluorescence, thus requiring increased dye concentrations. In PCR assays with conventional DNA polymerases, both blood and increased dye concentration are inhibitory. The compositions and methods described herein provide for the use of inhibition resistant mutant polymerase enzymes in real-time PCR applications with blood- or soil-containing samples with dye in PCR reaction mixtures.

Another aspect of the invention is the use of inhibition-resistant mutant DNA polymerase enzymes in standard (i.e., non-real time) PCR assays with crude samples containing, for example, blood, soil, or a combination of blood and soil.

Dye

One aspect of the invention provides a method for improving detection of a target nucleic acid in real-time PCR (qPCR) by using polymerase mutants (e.g., mutant Taq DNA polymerase or mutant Klentaq DNA polymerase) to overcome inhibitory effects of dyes (e.g., fluorescent dyes) used in qPCR.

A resistant polymerase can be used to amplify a DNA target in a real-time PCR of a DNA target in the presence of an inhibitory dye. A resistant polymerase can be used to amplify an RNA target in a real-time reverse transcriptase (RT) PCR of an RNA target in the presence of an inhibitory dye.

Figure 1A:
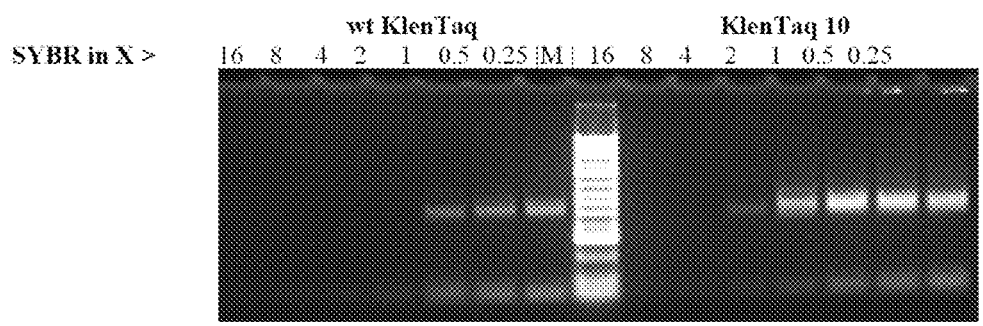
FIG. 1A-FIG. 1C are a series of images and graphs depicting results of PCR amplification of a 0.6 kbp *Bacillus cereus* target DNA with wild type KlenTaq and mutant KlenTaq 10 polymerases conducted in the presence of 7 twofold decreasing concentrations of SYBR Green.
Figure 1B:
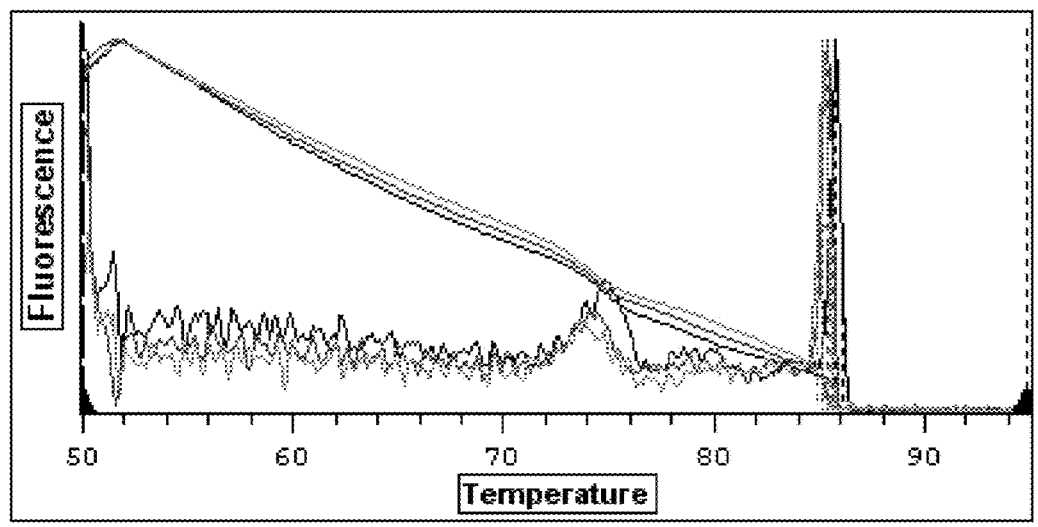
Figure 1C:
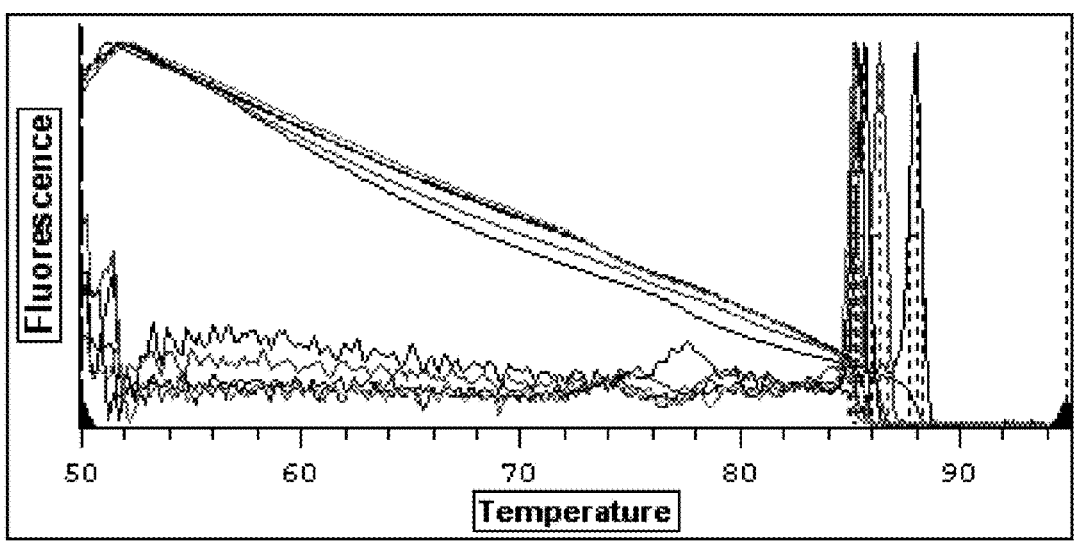
Figure 2A:
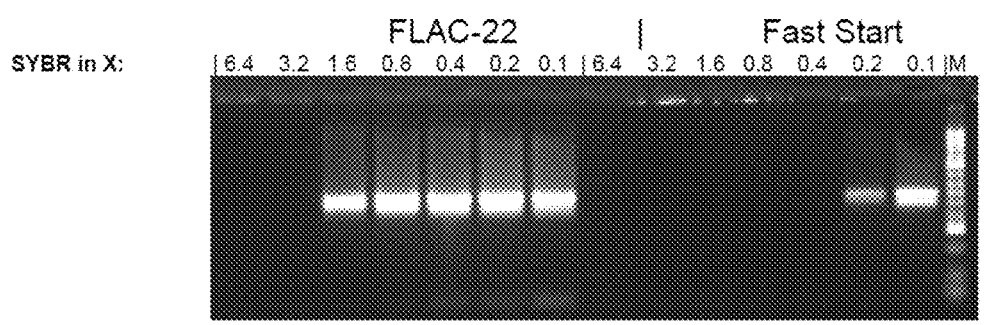
FIG. 2A-FIG. 2C are a series of images and graphs depicting results of PCR amplification of a 0.6 kbp *Bacillus cereus* target DNA with mutant FLAC-22 and a commercial enzyme, Fast Start, conducted in the presence of 7 twofold decreasing concentrations of SYBR Green.
Figure 2B:
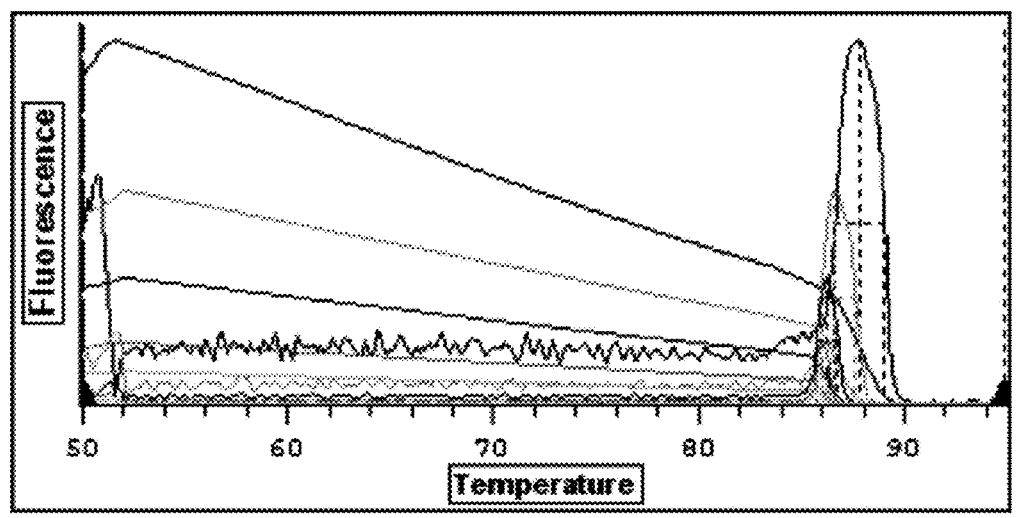
Figure 2C:
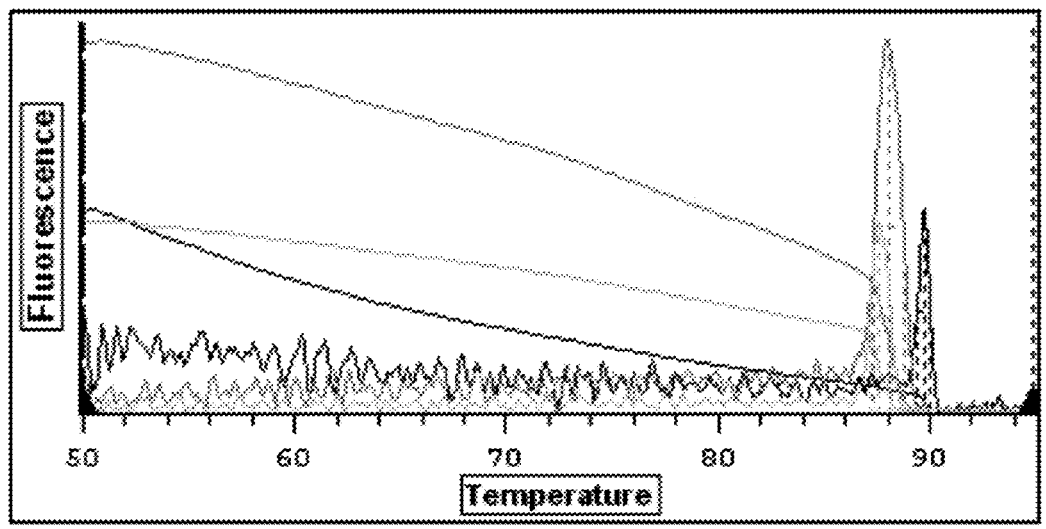
Figure 3A:
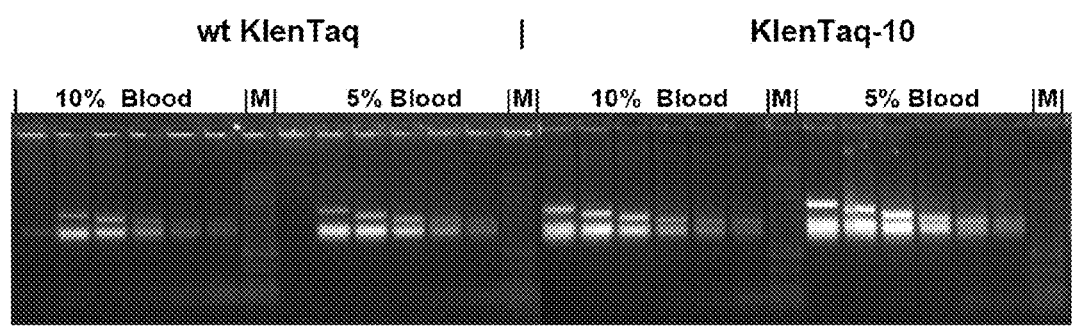
FIG. 3A-FIG. 3E are a series of images and graphs depicting results of PCR amplification of an exogenous 0.6 kbp *Bacillus cereus* target DNA with wild type KlenTaq and mutant KlenTaq10 polymerases in the presence of 5 and 10% blood in addition to very high concentrations of SYBR with subsequent decreasing amounts of SYBR.
Figure 3B:
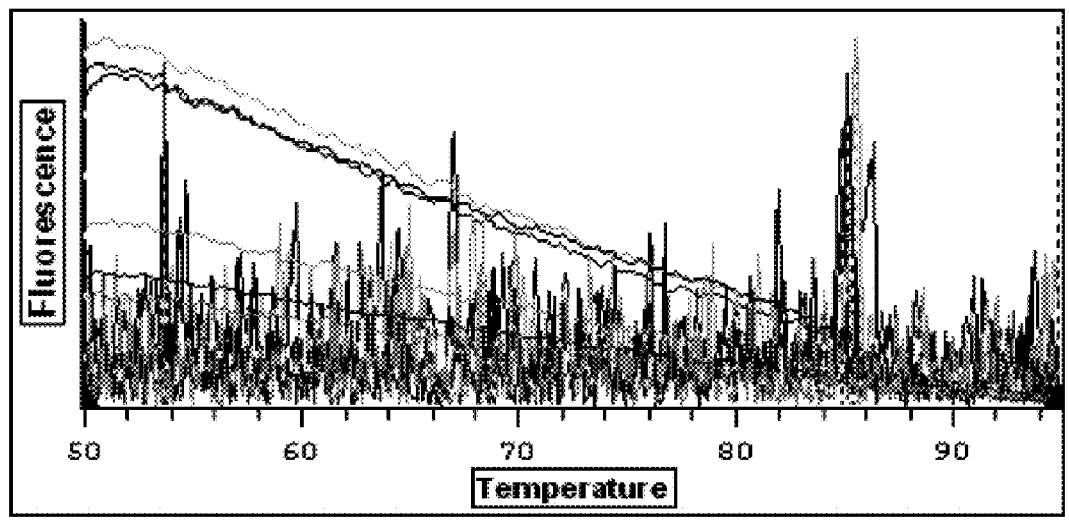
Figure 3C:
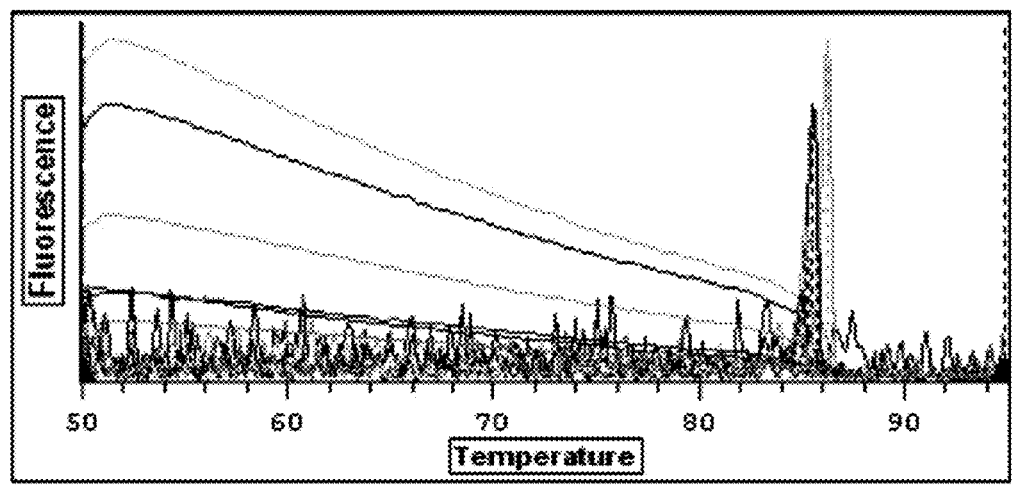
Figure 3D:
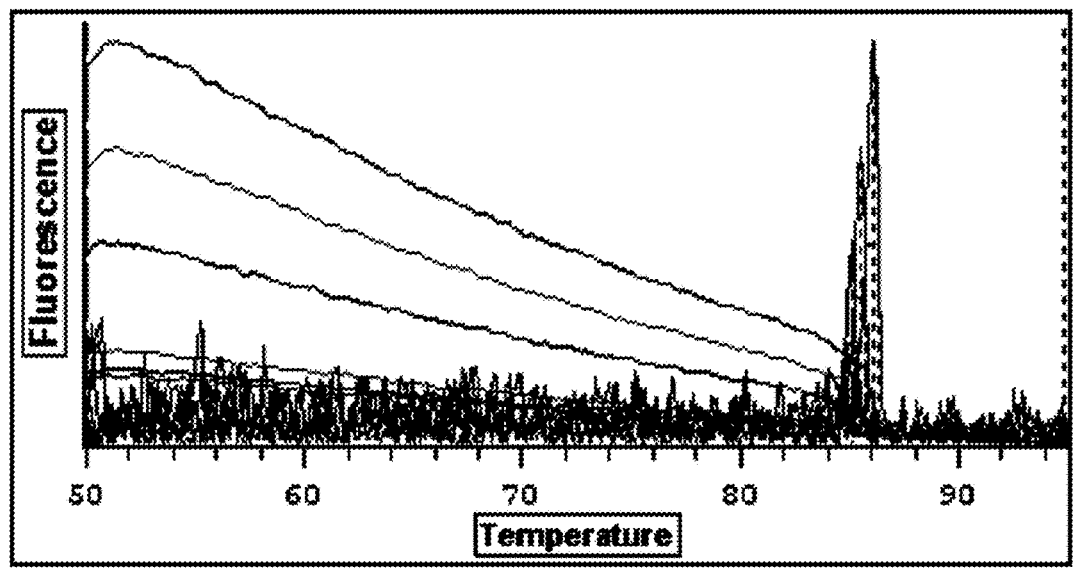
Figure 3E:
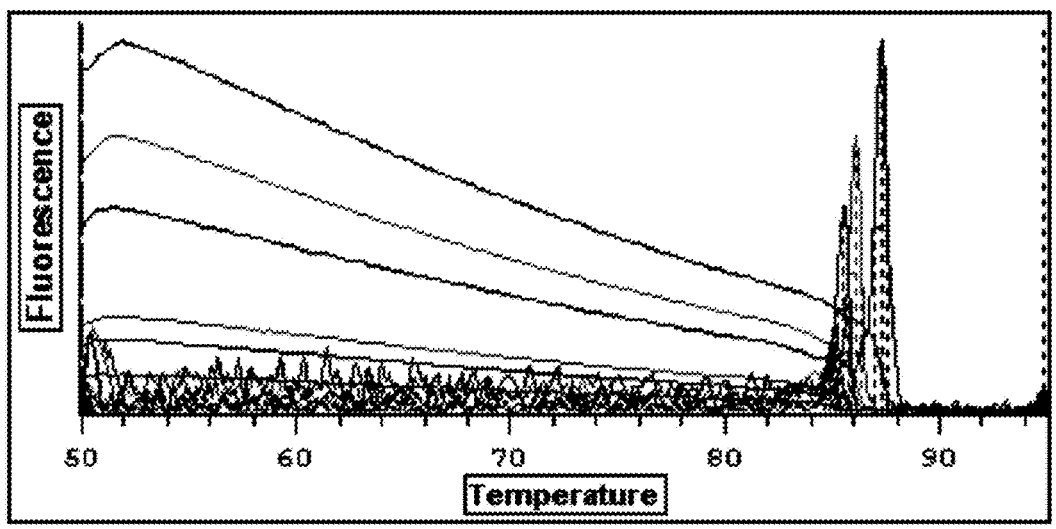

Dye-resistance can be readily determined by assays known in the art and described herein (see e.g., FIGS. 1, 2, and 8).

Various embodiments of the mutant polymerase enzymes described herein can tolerate increased concentrations of dyes. Such increased concentrations include, but are not limited to, up to about 0.5×, 1×, 1.5×, 2×, 2.5×, 3×, 3.5×, 4×, 4.5×, 5×, 5.5×, 6×, 6.5×, 7×, 7.5×, 8×, 8.5×, 9×, 9.5×, 10×, 15×, 20×, 25×, 30×, 35×, 40×, 45×, 50×, 55×, 60×, 65×, 70×, 80×, 90×, 100×, 150×, 200×, 250×, or even higher (see e.g., FIGS. 1A, 1B, 2A, 2B, 2C, and 8) over the dye concentration conventionally used in the assay. As an example, X can be the standard manufacturers unit for dye concentration provided in a commercial product (e.g., SYBR Green, Molecular Probes, Eugene, Oreg.). For example, for SYBR Green, X corresponds to a concentration of about 5 to about 10 μM.

Dye tolerance of a mutant polymerase enzyme (e.g., mutant Taq DNA polymerase) can provide, for example, higher amplification rate, higher fluorescent signal, and/or increased efficiency as compared to standard concentrations of dyes. Dye-tolerant mutant enzymes can improve the detection of the amplification target, especially when having low copy number of the nucleic acid target. As an additional benefit, higher dye inhibition resistance can permit enough dye (e.g., SYBR dye) in real time reactions to overcome the background fluorescence or quenching effect of PCR inhibitors, thus permitting detection of a target nucleic acid amongst inhibitors (e.g., components in blood and soil).

Dyes for use in the methods described herein include, but are not limited to, SYBR Green (Molecular Probes, Eugene, Oreg.), LC Green (Idaho Technology, Salt Lake City, Utah), PicoGreen (Molecular Probes, Eugene, Oreg.), TOTO (Molecular Probes, Eugene, Oreg.), YOYO (Molecular Probes, Eugene, Oreg.) and SYTO9 (Molecular Probes, Eugene, Oreg.).

With their tolerance to high dye concentrations, the mutant polymerases described herein can outperform other conventional polymerase enzymes, including top commercial PCR enzymes, with commercially available dyes used in qPCR including, but not limited to, SYBR Green (see e.g., FIGS. 1A, 2A, 2B, and 8)), LC Green (Idaho Technology, Salt Lake City, Utah), PICO, TOTO (Molecular Probes, Eugene, Oreg.), YOYO (Molecular Probes, Eugene, Oreg.), SYTO (Molecular Probes, Eugene, Oreg.), and ethidium bromide. Some of these dyes are even more inhibitory than SYBR Green to a conventional Taq enzyme in PCR.

Blood

In some embodiments, resistant polymerases described herein can amplify a target nucleic acid in the presence of blood or blood components. A resistant polymerase can be used to amplify a DNA target in a real-time PCR of a DNA target in the presence of blood or blood components. A resistant polymerase can be used to amplify an RNA target in a real-time reverse transcriptase (RT) PCR of an RNA target in the presence of blood or blood components.

Whole blood generally comprises plasma, serum, and blood cells. Blood components include, but are not limited to, red blood cells, white blood cells (e.g., leukocytes or platelets, i.e., thrombocytes), plasma, serum, hemoglobin, water, proteins, glucose, amino acids, fatty acids, mineral ions, hormones, carbon dioxide, urea, and lactic acid. Resistant polymerases described herein can be used in PCR to amplify a nucleic acid target in the presence of one or more such blood components.

Blood plasma is generally understood as a liquid suspension in which blood cells are circulated. Thus, blood plasma can include one or more of water, proteins, glucose, amino acids, fatty acids, mineral ions, hormones, carbon dioxide, urea, lactic acid, platelets (i.e., thrombocytes), and blood cells. In a human subject, blood plasma represents about 55% of whole blood, or about 2.7 to 3 liters in an average human subject. Blood plasma contains about 92% water, 8% blood plasma proteins, and trace amounts of other materials. Blood plasma can contain serum albumin, blood-clotting factors, immunoglobulins, lipoproteins, other proteins, and electrolytes (e.g., sodium and chloride). A crude sample comprising blood plasma can also contain blood cells. Resistant polymerases described herein can be used in PCR to amplify a nucleic acid target in the presence of blood plasma.

Blood serum is generally understood as plasma from which clotting proteins have been removed, leaving mostly albumin and immunoglobulins. Resistant polymerases described herein can be used in PCR to amplify a nucleic acid target in the presence of blood serum.

A blood-resistant polymerase, as that term is used herein, can generally display amplification activity in PCR assays (e.g., real-time PCR or real-time RT PCR) containing from about 1% to about 25% whole blood in the reaction mixture (vol/vol). For example, whole blood can comprise at least about 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, or 25% of a total volume of a PCR assay mixture comprising a blood-resistant polymerase described herein. In contrast, the full-length Taq enzyme (SEQ ID NO: 4) is usually completely inhibited in a blood concentration range of about 0.004% to about 0.2% whole blood in the reaction mixture (vol/vol).

A resistant polymerase, as described herein, can generally display amplification activity in PCR assays (e.g., real-time PCR or real-time RT PCR) containing from about 1% to about 25% of a blood component in the reaction mixture (vol/vol). For example, a blood component can comprise at least about 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, or 25% of a total volume of a PCR assay mixture comprising a blood-resistant polymerase described herein.

A resistant polymerase, as described herein, can generally display amplification activity in PCR assays (e.g., real-time PCR or real-time RT PCR) containing from about 1% to about 25% blood plasma in the reaction mixture (vol/vol). For example, blood plasma can comprise at least about 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, or 25% of a total volume of a PCR assay mixture comprising a blood-resistant polymerase described herein.

A resistant polymerase, as described herein, can generally display amplification activity in PCR assays (e.g., real-time PCR or real-time RT PCR) containing from about 1% to about 25% blood serum in the reaction mixture (vol/vol). For example, blood serum can comprise at least about 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, or 25% of a total volume of a PCR assay mixture comprising a blood-resistant polymerase described herein.

Blood-resistance can be readily determined by assays described herein and know in the art (see e.g., US Pat App Pub No 2006/0084074).

Soil

Various embodiments of the mutant DNA polymerases described herein are resistant to inhibitors found in soil and soil extracts.

In some embodiments, resistant polymerases described herein can amplify a target nucleic acid in the presence of an inhibitor found in soil or soil extract. A resistant polymerase can be used to amplify a DNA target in a real-time PCR of a DNA target in the presence of an inhibitor found in soil or soil extract. A resistant polymerase can be used to amplify an RNA target in a real-time reverse transcriptase (RT) PCR of an RNA target in the presence of an inhibitor found in soil or soil extract.

Soil inhibitors and soil extract inhibitors include, but are not limited to, humic acid, fulvic acid, polysaccarides, and metal ions. A soil-resistant polymerase, as that term is used herein, can generally display amplification activity in PCR assays containing from about 1% to about 90% soil or soil extract in the reaction mixture (vol/vol). For example, soil extract can comprise up to about 85%, 80%, 75%, 70%, 65%, 60%, 55%, 50%, 45%, 40%, 35%, 30%, 25%, 20%, 15%, 10%, 5%, or 1% of a total volume of a PCR assay mixture comprising a soil-resistant DNA polymerase described herein. For example, soil extract can comprise up to about 50%, 45%, 40%, 35%, 30%, 25%, 20%, 15%, 10%, 5%, or 1% of a total volume of a PCR assay mixture comprising a soil-resistant DNA polymerase described herein. The amount of soil or soil extract in the assay mixture can depend upon the levels of inhibitory substances in the soil or soil extract. Generally, the mutant DNA polymerases described herein can tolerate at least an order of magnitude greater concentration of these inhibitory substances, as compared to conventional DNA polymerases. Assays to determine the level of inhibitory substances in a sample are known in the art. Soil-resistance can be readily determined by assays described herein.

Direct extraction of total DNA from soil samples results in a co-extraction of humic acid, known as the most potent soil inhibitor to PCR analysis. Humic substances represent a mixture of partially characterized polyphenols that are produced during the decomposition of organic matter. Conventional DNA polymerase enzymes are inhibited at about 1 ng of humic acid per 50 uL reaction volume. Various embodiments of the mutant DNA polymerases described herein are resistant to soil or soil extract that contains, for example, various levels of humic acid. Preferably, the volume of soil or soil extract used in the PCR assay mixture is the soil or soil extract equivalent that provides up to about 25 ng of humic acid per 50 uL reaction volume. Assays to determine the amount of humic acid is a sample are known in the art. Preferably, the volume of soil or soil extract used in the PCR assay mixture is the soil or soil extract equivalent that provides up to about 20 ng of humic acid per 50 uL reaction volume, more preferably up to about 10 ng of humic acid per 50 uL reaction volume.

Combination

Preferably, the mutant polymerase enzymes are resistant to both blood and dye (e.g., fluorescent dye) inhibition; soil and dye inhibition; or blood, soil and dye inhibition, as might occur in, for example, a PCR reaction containing dye and blood and/or soil. Even more preferably, a synergy is provided in which the combination of the mutant enzymes, blood, and fluorescent dyes enable amplification and optical detection heretofore not possible. A preferred double inhibition resistant phenotype (i.e., blood and dye resistance) of a mutant enzyme makes possible the real-time detection of samples containing blood. Furthermore, in the presence of blood, the blood- and dye-resistant mutant polymerases can tolerate higher initial concentration of dye (e.g., tolerance of about 64× to about 256× for SYBR Green dye).

In some embodiments, resistant polymerases described herein can amplify a target nucleic acid in the presence of an inhibitory dye and an inhibitor found in soil or soil extract; an inhibitory dye and blood or a blood component; or an inhibitory dye, an inhibitor found in soil or soil extract, and blood or a blood component. A resistant polymerase can be used to amplify a DNA target in a real-time PCR of a DNA target in the presence of an inhibitory dye and an inhibitor found in soil or soil extract; an inhibitory dye and blood or a blood component; or an inhibitory dye, an inhibitor found in soil or soil extract, and blood or a blood component. A resistant polymerase can be used to amplify an RNA target in a real-time reverse transcriptase (RT) PCR of an RNA target in the presence of an inhibitory dye and an inhibitor found in soil or soil extract; an inhibitory dye and blood or a blood component; or an inhibitory dye, an inhibitor found in soil or soil extract, and blood or a blood component.

Interference between the blood and the fluorescent dye is demonstrated herein to at least partially eradicate the detection of the amplified product when using normal (i.e., low) dye concentrations (e.g., 1× or lower for SYBR Green). Adding high dye concentration to the reaction (allowed through the use of dye-resistant mutant polymerases described herein) can help to overcome the quenching effect of blood components (e.g., heme) on the dye fluorescence.

PCR

In some embodiments, a resistant polymerase can be employed in a real-time PCR amplification of a DNA target.

The DNA polymerases resistant to PCR inhibitors described herein can be used in a variety of polymerase reactions known to the art (see e.g., Dorak (2006) Real-Time PCR, Taylor & Francis, ISBN 041537734X; Bustin, ed. (2004) A-Z of Quantitative PCR, International University Line, ISBN 0963681788). For example, the resistant polymerases can be employed in PCR reactions, primer extension reactions, etc. The use of the mutant polymerase enzymes described herein generally does not require any, or substantial, changes in the typical protocol, other than, for example, adding higher amounts of fluorescent dye. Thus, methods described herein can be applied to improve the nucleic acid detection in any standard real-time PCR with purified template nucleic acids and primers.

In some embodiments, a resistant polymerase can be employed in a real-time reverse transcriptase (RT) PCR amplification of an RNA target. It is noted that reverse transcriptase (RT) PCR is not to be confused with real-time polymerase chain reaction (Q-PCR), which is sometimes (incorrectly) abbreviated as RT-PCR in the art. In RT-PCR, an RNA strand is first reverse transcribed into its DNA complement (complementary DNA, or cDNA) using the enzyme reverse transcriptase, and the resulting cDNA is amplified using traditional PCR. Like with standard PCR, conventional RT-PCR protocols require extensive purification steps prior to amplification to purify RNA from inhibitors and ribonucleases, which can destroy the RNA template. Both the inhibition and degradation of RNA are major concerns in important clinical and diagnostics tests, which may lead to false-negative results.

Applications of RT-PCR include, but are not limited to, detection of RNA virus pathogens; analysis of mRNA expression patterns of certain genes related to various diseases; semiquantitative determination of abundance of specific different RNA molecules within a cell or tissue as a measure of gene expression; and cloning of eukaryotic genes in prokaryotes.

Resistant polymerases described herein can be used in a variety of RT-PCR protocols known to the art (see e.g., King and O'Connel (2002) RT-PCR Protocols, 1$^{st}$ Ed., Human Press, ISBN-10 0896038750). The use of the mutant polymerase enzymes described herein generally does not require any, or substantial, changes in the typical protocol, other than, for example, adding higher amounts of a fluorescent dye. Thus, methods described herein can be applied to improve target detection in any standard RT PCR.

The buffer for use in the various PCR assay mixtures described herein is generally a physiologically compatible buffer that is compatible with the function of enzyme activities and enables cells and/or biological macromolecules to retain their normal physiological and biochemical functions. Typically, a physiologically compatible buffer will include a buffering agent (e.g., TRIS, MES, PO$_4$, HEPES, etc.), a chelating agent (e.g., EDTA, EGTA, or the like), a salt (e.g., ammonium sulfate, NaCl, KCl, MgCl.sub.2, CaCl.sub.2, NaOAc, KOAc, Mg(OAc).sub.2, etc.) and optionally a stabilizing agent (e.g., sucrose, glycerine, Tween20, etc.).

Various PCR additives and enhancers can be employed with the methods described herein. For example, betaine can be added to the PCR assay, to further aid in overcoming the inhibition by blood and/or soil. Betaine can be included at final concentration about 1 M to about 2M. Generally, betaine alone is insufficient to overcome the inhibition of, for example, dye, blood, and/or soil when used with conventional DNA polymerases.

Mutant Polymerases

Examples of mutant enzymes useful to the invention include, but are not limited to, KlenTaq-10 (SEQ ID NO: 1) (as described in US Pat App Pub No 2006/0084074, specifically incorporated herein by reference in its entirety) and the full-length Taq enzyme mutant, FLAC-22 (SEQ ID NO: 2), as well as variant polypeptides of these reference sequences, as described below.

For the following discussion, wild type Taq numbering is used in this descriptive text so as to make clear the relationship between the polypeptides. For truncated polymerase polypeptides (e.g., Klentaq-10 of SEQ ID NO: 1; Klentaq-1 of SEQ ID NO: 3), position number 1 as notated in the Sequence Listing of SEQ ID NO: 1 or SEQ ID NO: 3 corresponds to position number 279 as notated in the full-length Taq of SEQ ID NO: 4. Similarly, position number 2 of SEQ ID NO:1 or SEQ ID NO: 3 corresponds to position number 280 of SEQ ID NO: 4.

KlenTaq-1 (SEQ ID NO: 3) has an N-terminal deletion at 278 of a full-length Taq (SEQ ID NO: 4), with Met/Gly replacing amino acids 279 and 280 (per wild type Taq numbering). It is noted that Klentaq-1 is a "wild-type" Klentaq given that it is directly derived from wild-type Taq by truncation.

KlenTaq-10 (SEQ ID NO: 1) has an N-terminal deletion at 278 of a full-length wild type Taq (SEQ ID NO: 4) and substitutions at E626K, I707L, and E708K (per wild type Taq numbering).

FLAC22 (SEQ ID NO: 2) is a full-length Taq (SEQ ID NO: 4) with substitutions at E626K, I707L, and E708N (per wild type Taq numbering).

Also included in the scope of the invention are variant polypeptides (or encoding polynucleotides) with at least 80% sequence identity to the above-described sequences, so long as such variants retain dye-resistant polymerase activity; dye- and blood-resistant polymerase activity; dye- and soil-resistant polymerase activity; or dye-, blood-, and soil-resistant polymerase activity. For example, variant polypeptides (or encoding polynucleotides) with dye-resistant polymerase activity; dye- and blood-resistant polymerase activity; dye- and soil-resistant polymerase activity; or dye-, blood-, and soil-resistant polymerase activity can have at least about 85%, 86%, 87%, 88%, 89%, 90%, 91%, 92%, 93%, 94%, 95%, 96%, 97%, 98%, 99%, or 99.9% sequence identity to sequences disclosed herein. Preferably, variant polypeptides (or encoding polynucleotides) with dye-resistant polymerase activity; dye- and blood-resistant polymerase activity; dye- and soil-resistant polymerase activity; or dye-, blood-, and soil-resistant polymerase activity have at least 95% sequence identity to sequences disclosed herein. More preferably, variant polypeptides (or encoding polynucleotides) with dye-; dye- and blood-; dye- and soil-; or dye-, blood- and soil-resistant polymerase activity have at least 99% sequence identity to sequences disclosed herein. The species of SEQ ID NO: 1 and SEQ ID NO: 2 are representative of the genus of variant polypeptides of each of these respective sequences because all variants must possess the specified catalytic activity (e.g., dye-, blood-, and/or soil-resistant polymerase activity) and must have the percent identity required above to the reference sequence.

Design, generation, and testing of the variant polypeptides having the above required percent identities to the sequences of the mutant DNA polymerases and retaining a required resistant phenotype is within the skill of the art. For example, directed evolution and rapid isolation of mutants can be according to methods described in references including, but not limited to, Link et al. (2007) Nature Reviews 5(9), 680-688; Sanger et al. (1991) Gene 97(1), 119-123; Ghadessy et al. (2001) Proc Natl Acad Sci USA 98 (8) 4552-4557. Thus, one skilled in the art could generate a large number of polypeptide variants having, for example, at least 95-99% identity to the sequences of mutant DNA polymerases described herein and screen such for phenotypes including, dye-resistance, blood-resistance, and/or soil-resistance according to methods routine in the art. Generally, conservative substitutions can be made at any position so long as the required activity is retained. Amino acid positions known to be associated with the phenotypes described herein include, but are not limited to 626, 707, and 708 (per wild type Taq numbering) (see Example 9). For example, preferred substitutions at 708 include K and L for truncated and full length mutant Taq polymerases; N, Q, and I for full length mutant Taq polymerases; and W in truncated mutant Taq polymerases. Preferable substitutions include E708R and E708L.

Amino acid sequence identity percent (%) is understood as the percentage of amino acid residues that are identical with amino acid residues in a candidate sequence in comparison to a reference sequence when the two sequences are aligned. To determine percent amino acid identity, sequences are aligned and if necessary, gaps are introduced to achieve the maximum percent sequence identity; conservative substitutions are not considered as part of the sequence identity. Amino acid sequence alignment procedures to determine percent identity are well known to those of skill in the art. Often publicly available computer software such as BLAST, BLAST2, ALIGN2 or Megalign (DNASTAR) software is used to align peptide sequences. Those skilled in the art can determine appropriate parameters for measuring alignment, including any algorithms needed to achieve maximal alignment over the full-length of the sequences being compared. When amino acid sequences are aligned, the percent amino acid sequence identity of a given amino acid sequence A to, with, or against a given amino acid sequence B (which can alternatively be phrased as a given amino acid sequence A that has or comprises a certain percent amino acid sequence identity to, with, or against a given amino acid sequence B) can be calculated as: percent amino acid sequence identity=X/Y100, where X is the number of amino acid residues scored as identical matches by the sequence alignment program's or algorithm's alignment of A and B and Y is the total number of amino acid residues in B. If the length of amino acid sequence A is not equal to the length of amino acid sequence B, the percent amino acid sequence identity of A to B will not equal the percent amino acid sequence identity of B to A.

Mutant DNA polymerases described herein can be produced according to methods known in the art. For example, oligonucleotides providing the specific amino acid changes to a mutant DNA polymerase described can be prepared by standard synthetic techniques (e.g., an automated DNA synthesizer) and used as PCR primers in site-directed mutagenesis. Standard procedures of expression of mutant DNA polymerase polypeptides from encoding DNA sequences can then be performed. Alternatively, the mutant DNA polymerase polypeptides can be directly synthesized according to methods known in the art.

Having described the invention in detail, it will be apparent that modifications, variations, and equivalent embodiments are possible without departing the scope of the invention defined in the appended claims. Furthermore, it should be appreciated that all examples in the present disclosure are provided as non-limiting examples. Furthermore, it should be appreciated that all examples in the present disclosure are provided as non-limiting examples.

EXAMPLES

The following non-limiting examples are provided to further illustrate the present invention. It should be appreciated by those of skill in the art that the techniques disclosed in the examples that follow represent approaches the inventors have found function well in the practice of the invention, and thus can be considered to constitute examples of modes for its practice. However, those of skill in the art should, in light of the present disclosure, appreciate that many changes can be made in the specific embodiments that are disclosed and still obtain a like or similar result without departing from the spirit and scope of the invention. It shall be understood that any method described in an example may or may not have been actually performed, or any composition described in an example may or may not have been actually been formed, regardless of verb tense used.

Example 1

The following primer oligonucleotides were used in real-time PCR reaction to amplify a 0.6 kbp *Bacillus cereus* specific target from 20 pg input genomic DNA: forward 5'-AGG GTC ATT GGA AAC TGG G-3' (SEQ ID NO 5), and reverse 5'-CGT GTT GTA GCC CAG GTC ATA-3' (SEQ ID NO 6). The final concentration of each primer was 0.2 uM used in a common master mix. The amount of each enzyme used was 2.5 units per 50 ul reaction. Wild type KlenTaq and mutant KlenTaq-10 were challenged with a series of seven two-fold SYBR green fluorescent dye dilutions starting with 16× concentration. After 40 cycles the products were analyzed both in 2% agarose gel electrophoresis (see e.g., FIG. 1A) and temperature dissociation profile (see e.g., FIG. 1B).

Results show that KlenTaq-10 was capable of amplifying a 0.6 kbp *Bacillus cereus* target DNA in the presence of 4×SYBR, while the wild type failed at concentrations higher than 1× (see e.g., FIG. 1). The post PCR melting curve analysis confirms the fluorescent detection and the specificity of the product.

Example 2

The following primer oligonucleotides were used in real-time PCR reaction to amplify a 0.6 kbp *Bacillus cereus* specific target from 20 pg input genomic DNA: forward 5'-AGG GTC ATT GGA AAC TGG G-3' (SEQ ID NO 5), and reverse 5'-CGT GTT GTA GCC CAG GTC ATA-3' (SEQ ID NO 6). The final concentration of each primer was 0.2 uM used in a common master mix. The amount of each enzyme used was 2.5 units per 50 ul reaction. FLAC-22 (SEQ ID NO: 2) and Fast Start Tags were challenged with a series of seven two-fold SYBR green fluorescent dye dilutions starting with 6.4× concentration. After 40 cycles the products were analyzed both in 2% agarose gel electrophoresis (see e.g., FIG. 2A) and temperature dissociation profile (see e.g., FIG. 2B).

Results showed that FLAC-22 (SEQ ID NO: 2) was capable of amplifying a 0.6 kbp *Bacillus cereus* target DNA in the presence of 1.6×SYBR, while Fast Start Taq failed at concentrations higher than 0.2× (see e.g., FIG. 3). Post PCR melting curve analysis confirms the fluorescent detection and the specificity of the product.

Example 3

The following primer oligonucleotides were used in real-time PCR reaction to amplify a 0.6 kbp *Bacillus cereus* specific target from 20 pg input genomic DNA: forward 5'-AGG GTC ATT GGA AAC TGG G-3' (SEQ ID NO: 5), and reverse 5'-CGT GTT GTA GCC CAG GTC ATA-3' (SEQ ID NO: 6). The final concentration of each primer was 0.2 uM used in a common master mix. The amount of each enzyme used was 2.5 units per 50 ul reaction. Wild-type KlenTaq and KlenTaq-10 were double challenged with two blood concentrations 5% and 10% of the total reaction volume and with series of six two-fold SYBR green fluorescent dye dilutions starting with 64× concentration. After 40 cycles, the products were analyzed both in 2% agarose gel electrophoresis (see e.g., FIG. 3A) and temperature dissociation profile (see e.g., FIG. 3B).

Under normal circumstances, i.e., without blood, these conditions would be very inhibitory. But the results herein show that KlenTaq 10 was capable of amplifying with at least two times higher concentration of SYBR compared to the wild type KlenTaq (see e.g., FIG. 3). The post PCR melting curve analysis confirms that in the presence of 10% blood, at least 8×SYBR green is necessary for real-time PCR detection and at least 2×SYBR for 5% blood samples. Results also show that the resistance of KlenTaq 10 toward SYBR green is increased to at least 64× compared to 4× when there is no blood in the reaction.

Example 4

Figure 4A:
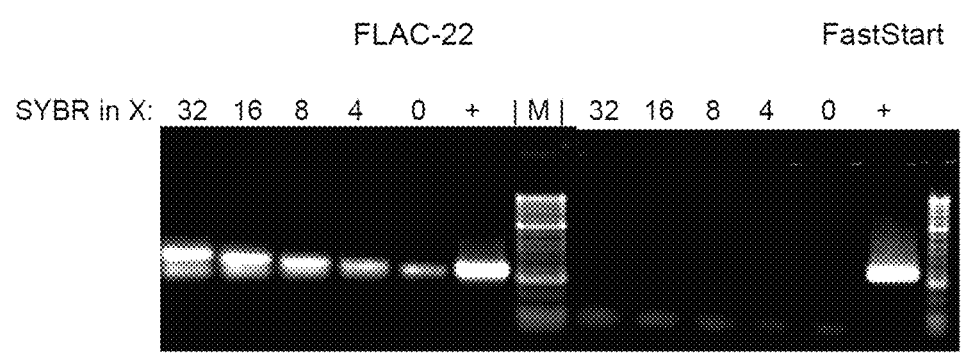
FIG. 4A-FIG. 4C are a series of images and graphs depicting results of PCR amplification of an exogenous 0.32 kbp 16S microbial target DNA with FLAC-22 and Fast Start Taq polymerases in the presence of constant 5% blood (excluding the positive control) and decreasing amounts SYBR green.
Figure 4B:
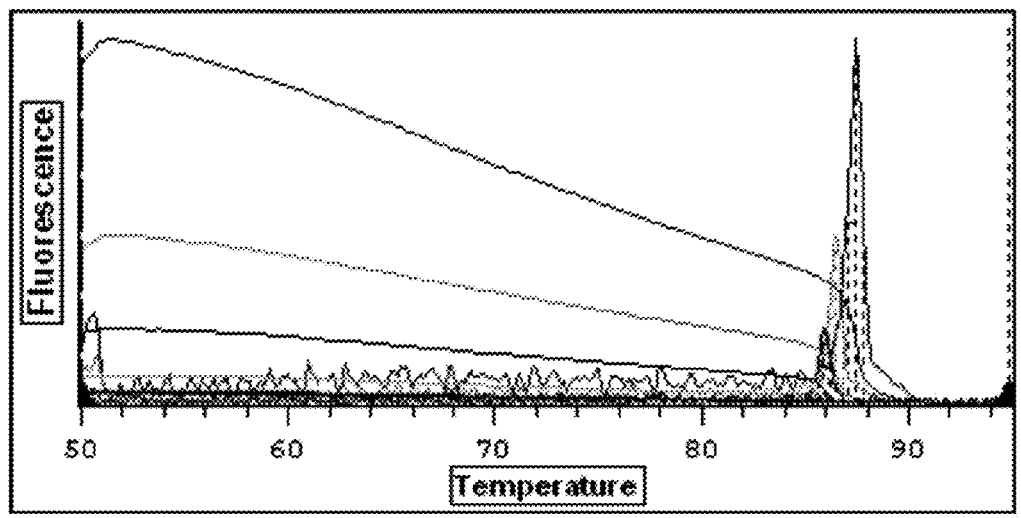

The following primer oligonucleotides were used in real-time PCR reaction to amplify a 0.32 kbp 16S microbial target: forward 5'-GGA TGC AAG CGT TAT CCG GAA TG-3' (SEQ ID NO 7), and reverse 5'-CAT TCT TGC GAA CGT ACT CCC CA-3' (SEQ ID NO 8). The final concentration of each primer was 0.2 uM used in a common master mix. The amount of each enzyme used was 2.5 units per 50 ul reaction. FLAC-22 (SEQ ID NO: 2) and Fast Start Tags were double challenged with 5% blood and with a series of four two-fold SYBR green fluorescent dye dilutions and no SYBR control starting with 32× concentration. A positive control, a reaction containing neither blood nor SYBR, was also included. After 40 cycles, the products were analyzed both in 2% agarose gel electrophoresis (see e.g., FIG. 4A) and temperature dissociation profile (see e.g., FIG. 4B).

Figure 4C:
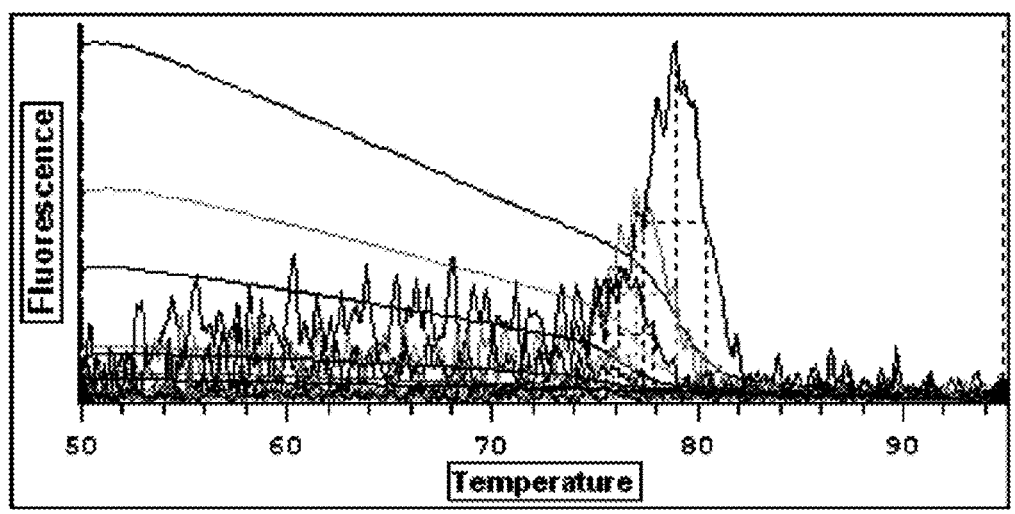

Without blood, these SYBR concentrations would be very inhibitory. But the results herein show that FLAC-22 (SEQ ID NO: 2) was capable of amplifying with all SYBR concentrations whereas Fast Start was inhibited by both blood and SYBR and was able to amplify only the positive control, containing neither blood nor dye (see e.g., FIG. 4). The post PCR melting curve analysis demonstrates that in the presence of 5% blood, at least 4×SYBR green is necessary for real-time PCR detection for FLAC-22 (SEQ ID NO: 2) while the Fast Start samples did do not show the correct melting temperature of the product at all. Once again, the resistance of FLAC-22 (SEQ ID NO: 2), toward SYBR green has increased to at least 32× compared to 2× without blood in the reaction.

Example 5

Figure 5A:
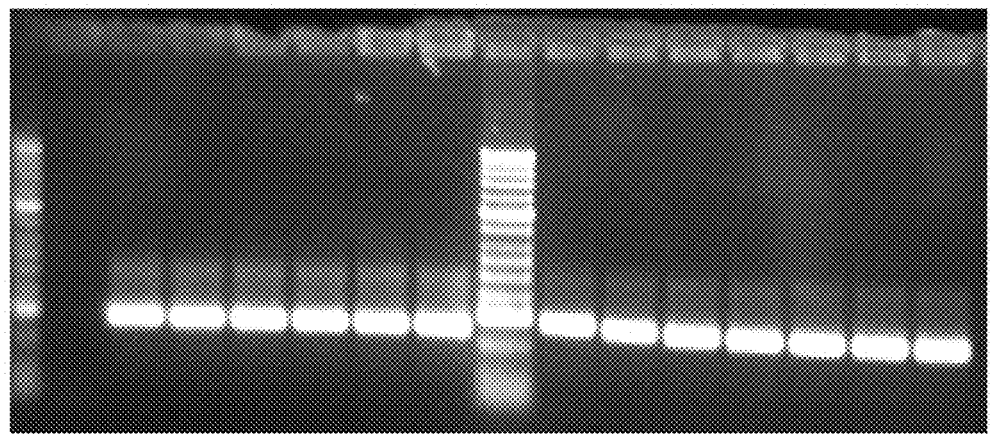
FIG. 5A-FIG. 5H are a series of images and graphs depicting results of PCR amplification with FLAC-22, KlenTaq-10, Fast Start, Jump Start, and AmpliTaq Gold Taq polymerases in the presence of 6 two-fold decreasing concentrations of SYBR green.
Figure 5B:
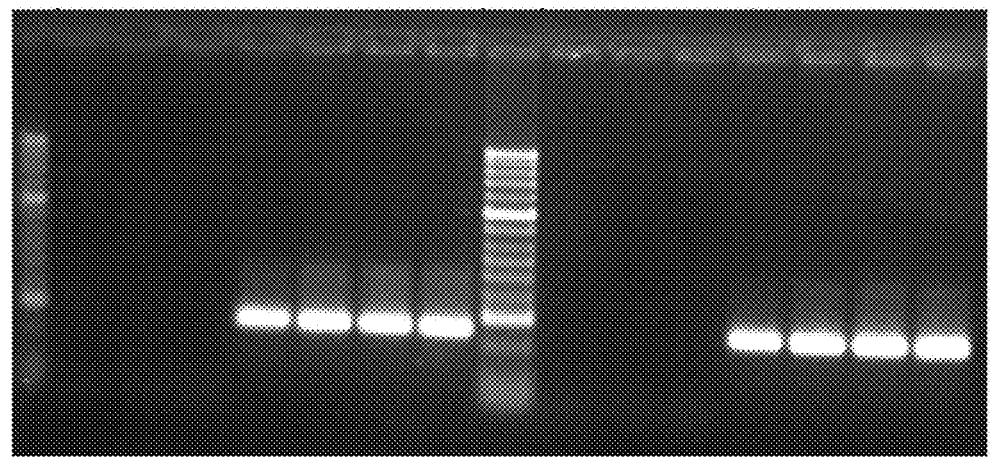
Figure 5C:
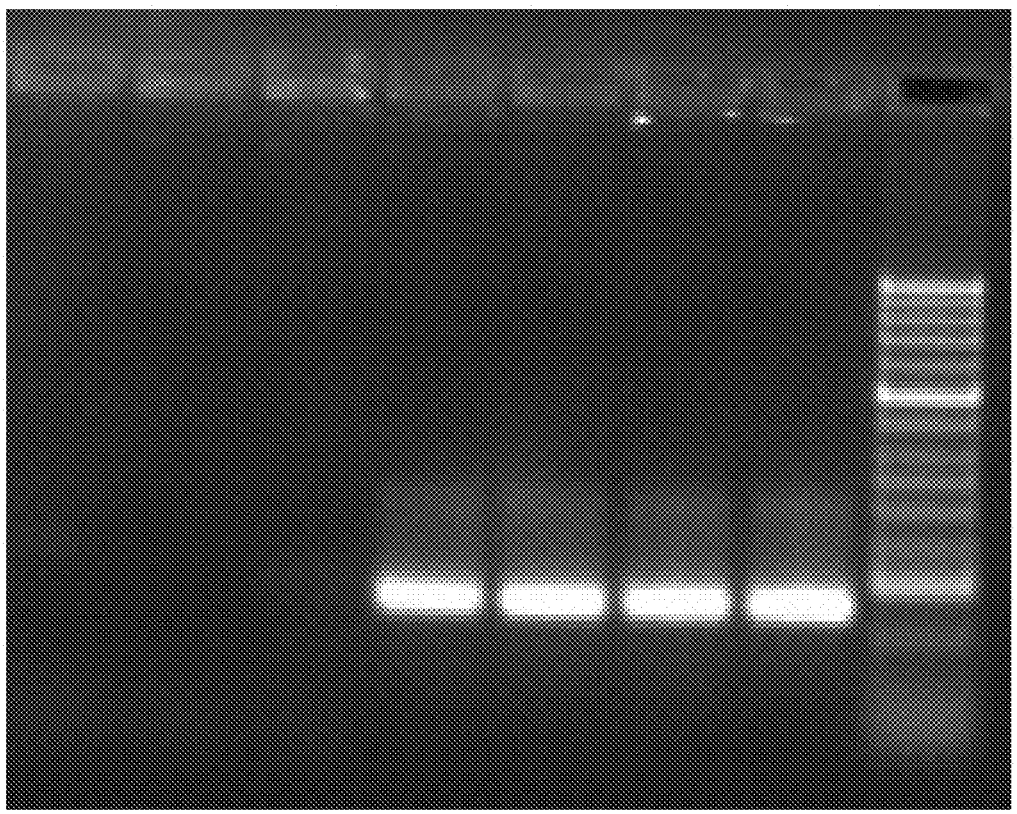
Figure 5D:
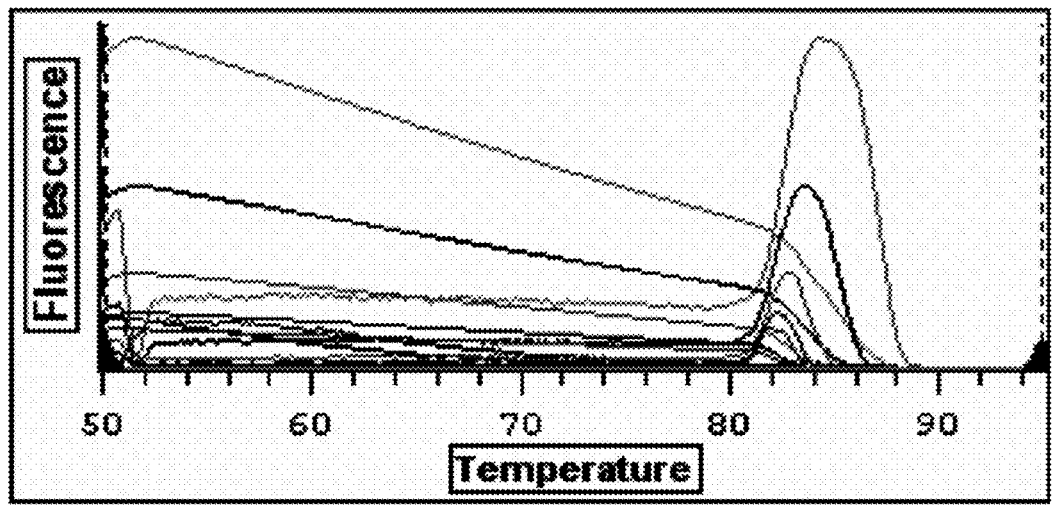
Figure 5E:
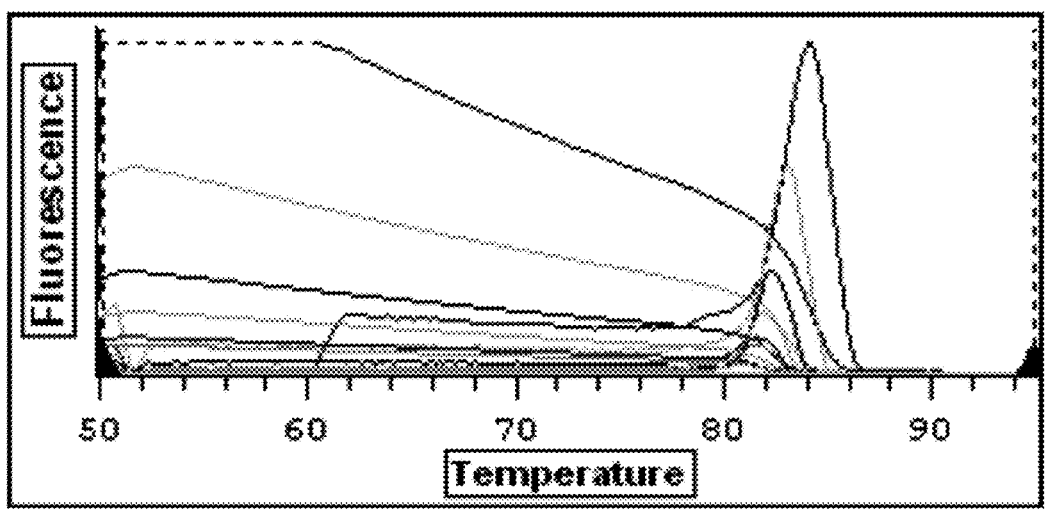
Figure 5F:
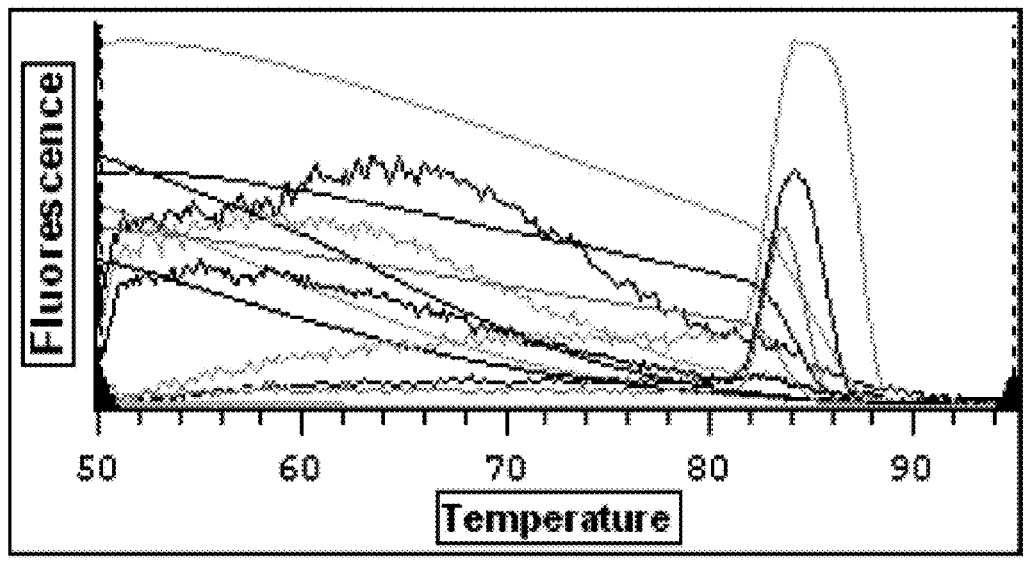
Figure 5G:
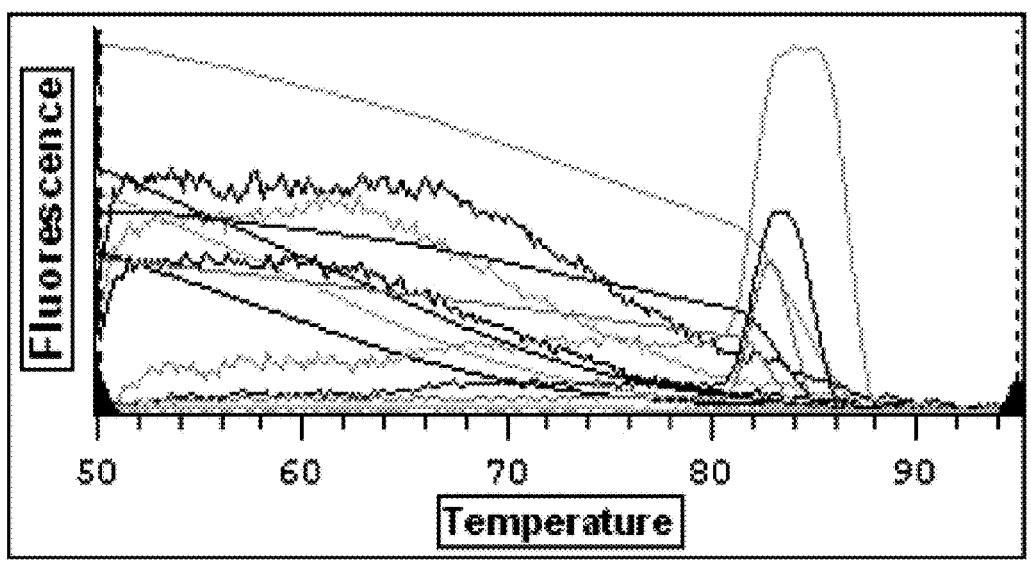
Figure 5H:
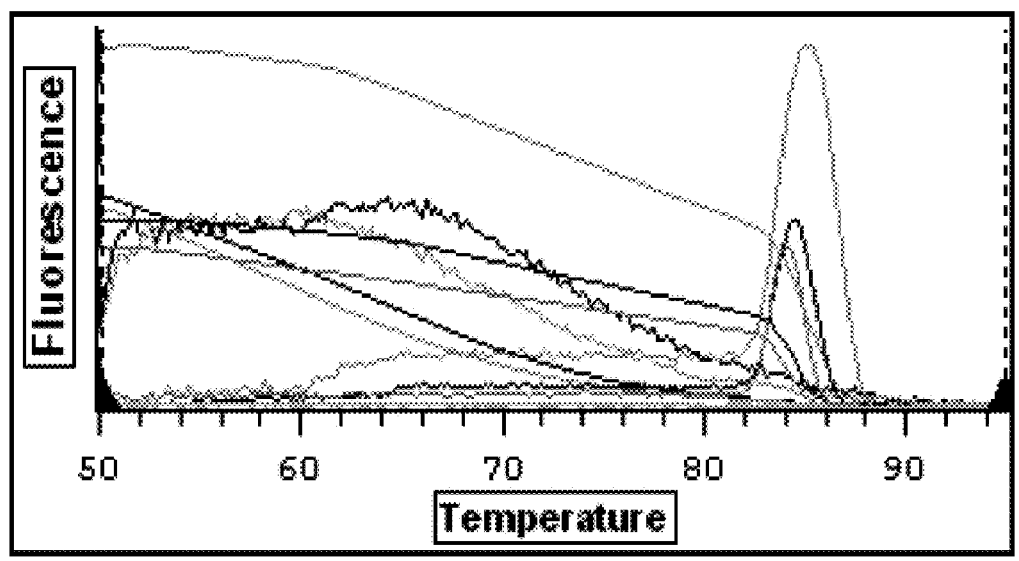
Figure 6A:
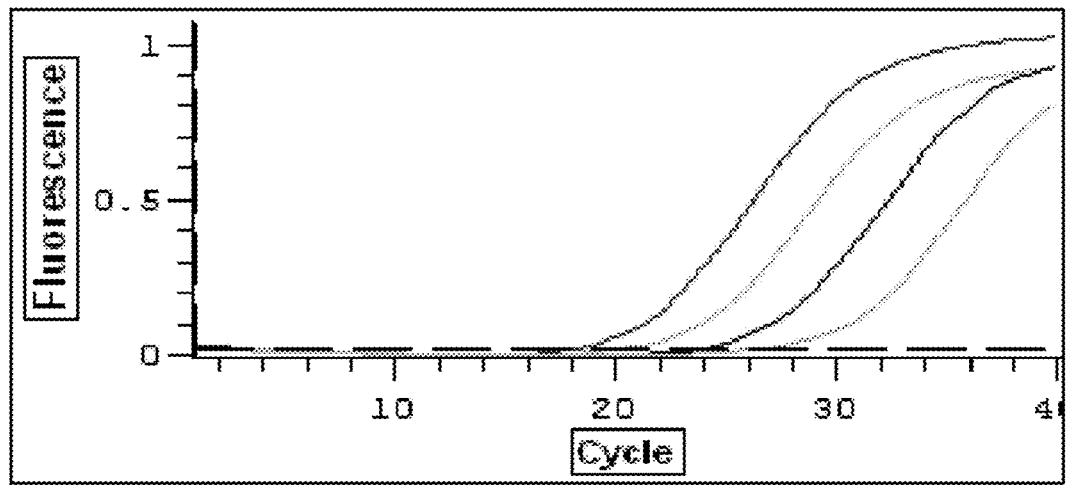
FIG. 6A-FIG. 6C are a series of graphs illustrating a successful real-time PCR detection of an anthrax genome target (1.3 kb *Bacillus anthracis*) at 5-fold dilutions in 5% human blood, with FLAC-22 mutant enzyme, using 32×SYBR Green concentration to compensate for the quenching effect of blood on the fluorescent dye.
Figure 6B:
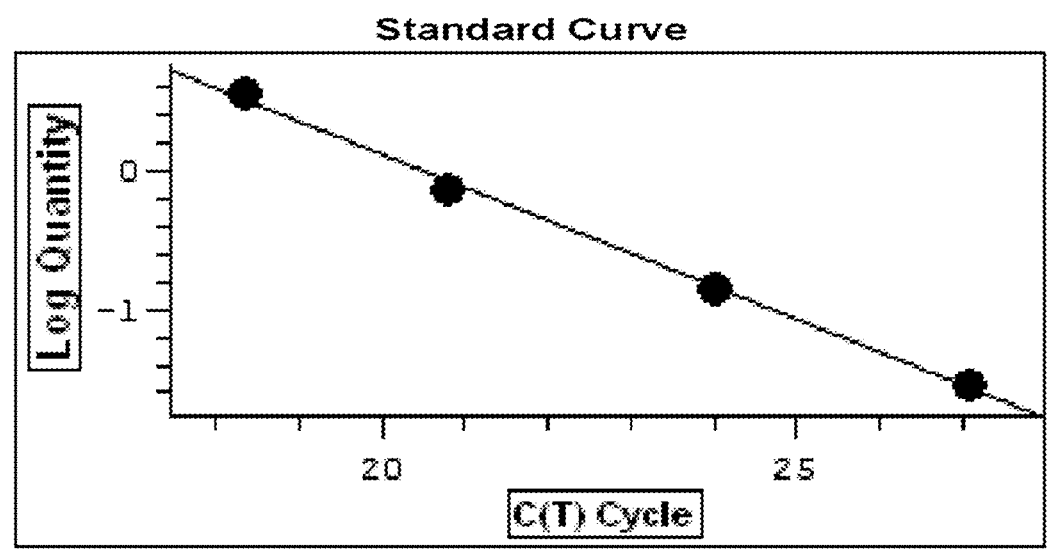
Figure 6C:
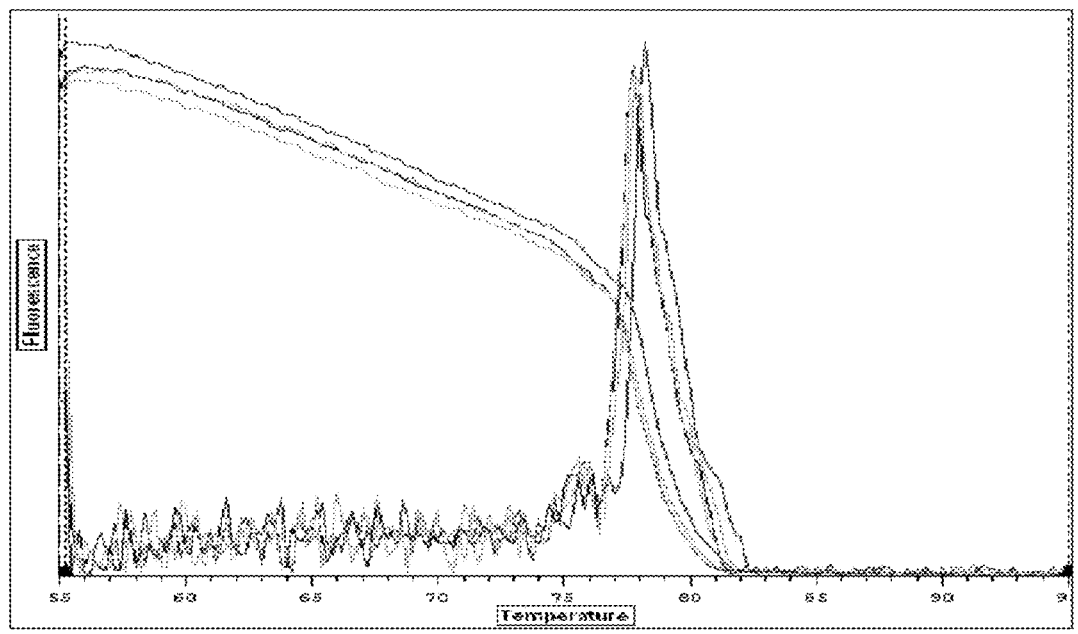

The following primer oligonucleotides were used in real-time PCR reaction to amplify a 0.25 kbp Lambda specific target: forward 5'-GGG CGG CGA CCT CGC GGG TTT TCG C-3' (SEQ ID NO 9), and reverse 5'-CTG AAT GGT ACG GAT ACT CGC ACC G-3' (SEQ ID NO 10). The final concentration of each primer was 0.2 uM used in a common master mix. The amount of each enzyme used was 2.5 units per 50 ul reaction. FLAC-22 (SEQ ID NO: 2), KlenTaq-10, Fast Start, JumpStart and AmpliTaq Gold polymerases were challenged with a series of seven two-fold SYBR green fluorescent dye dilutions starting with 4× concentration. After 35 cycles the products were analyzed both in 2% agarose gel electrophoresis (see e.g., FIG. 5A) and temperature dissociation profile (see e.g., FIG. 5B).

Results showed that FLAC-22 (SEQ ID NO: 2) was capable of amplifying a 0.25 kbp lambda target from added purified DNA template in the presence of 2×SYBR; and KlenTaq-10 was able to amplify with at least 4×SYBR; but the commercial Taq polymerases failed at concentrations higher than 0.5× (see e.g., FIG. 5). The post PCR melting curve analysis confirms the fluorescent detection and the specificity of the product.

Example 6

Whole human blood was pre-mixed with *Bacillus anthracis* DNA and subjected directly to PCR. Klentaq-10 specifically amplified the target in 5% blood, as indicated by the melting curve profile. In addition, the quantitation curves were highly proportional to the input amount of DNA so that the standards followed the general curve. High concentration of SYBR Green, 32×, was used to compensate for the quenching effect of blood on the fluorescent dye.

Example 7

Figure 7A:
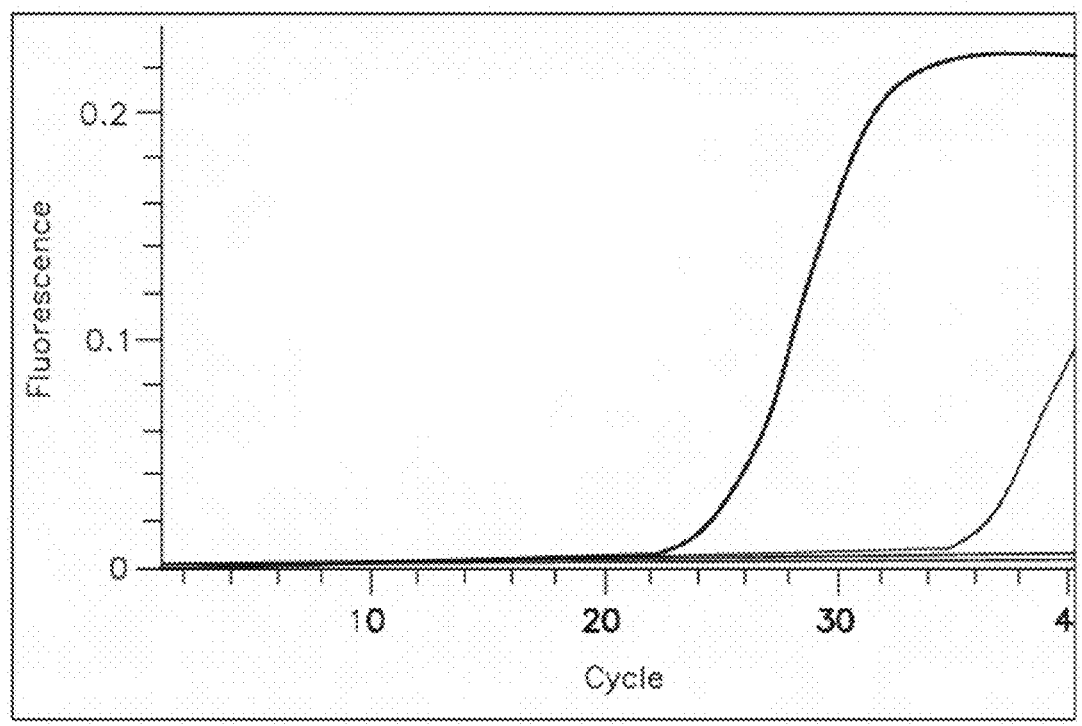
Figure 7B:
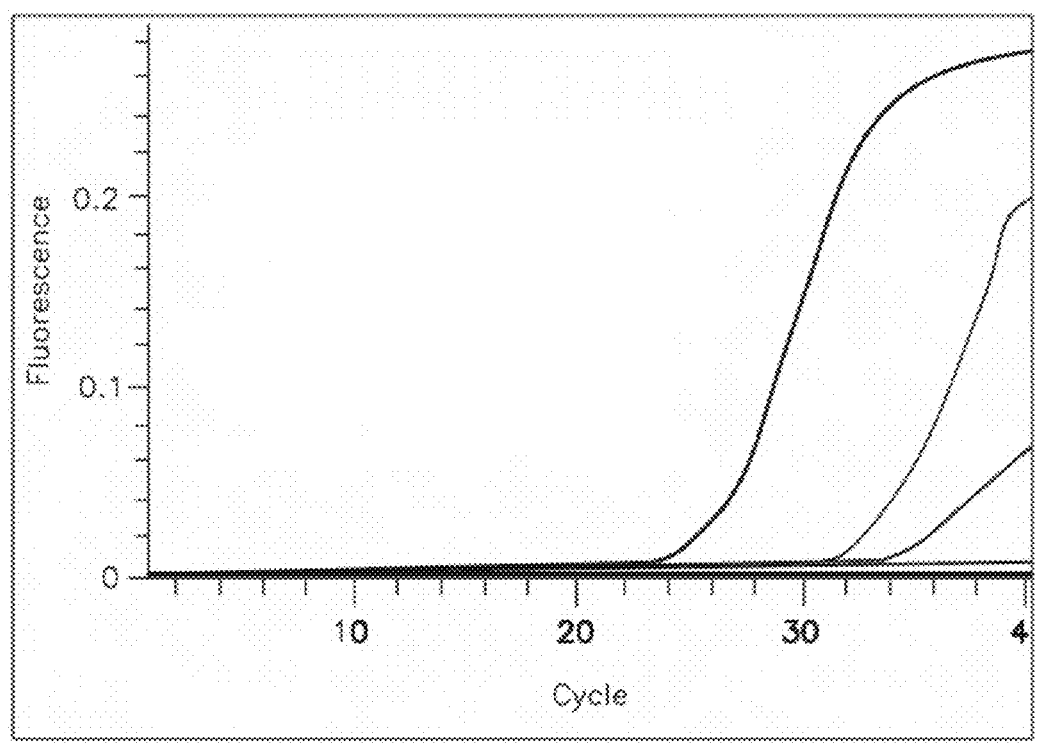
Figure 7C:
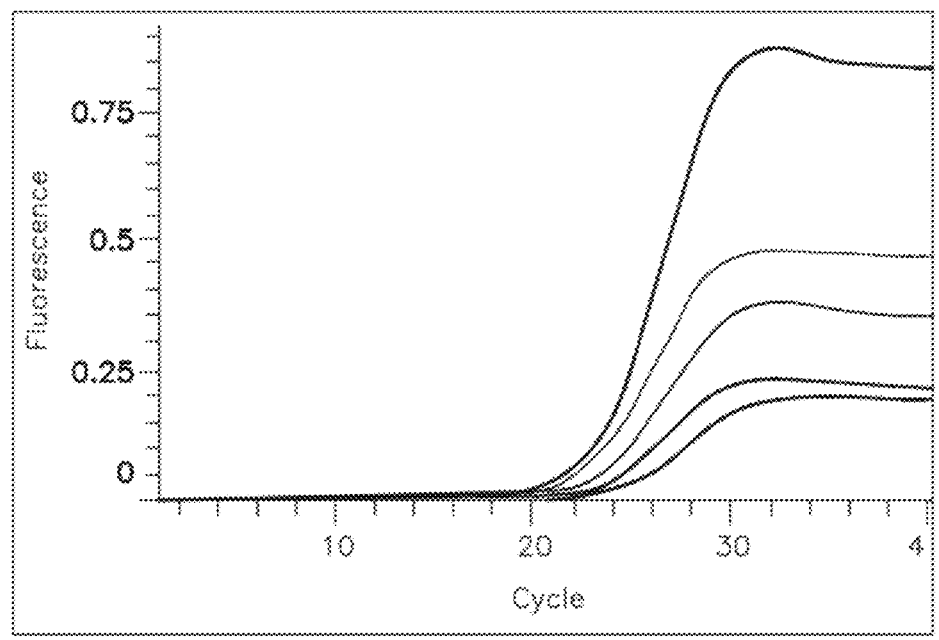
Figure 7D:
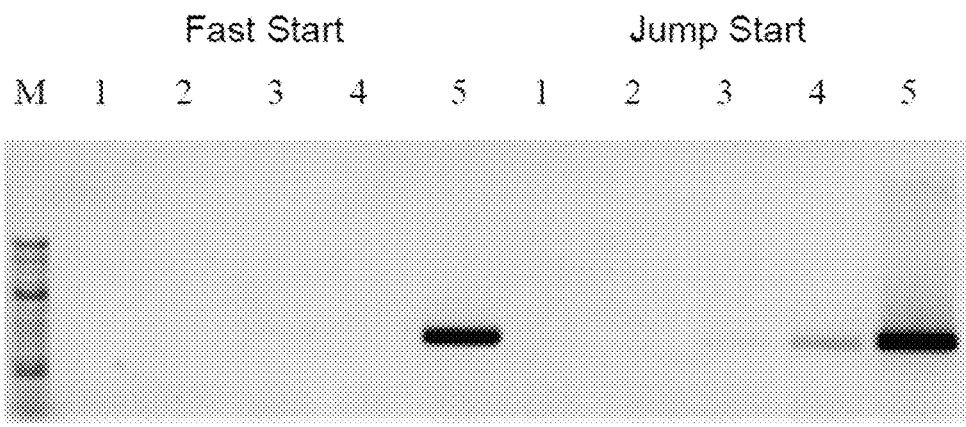
Figure 7E:
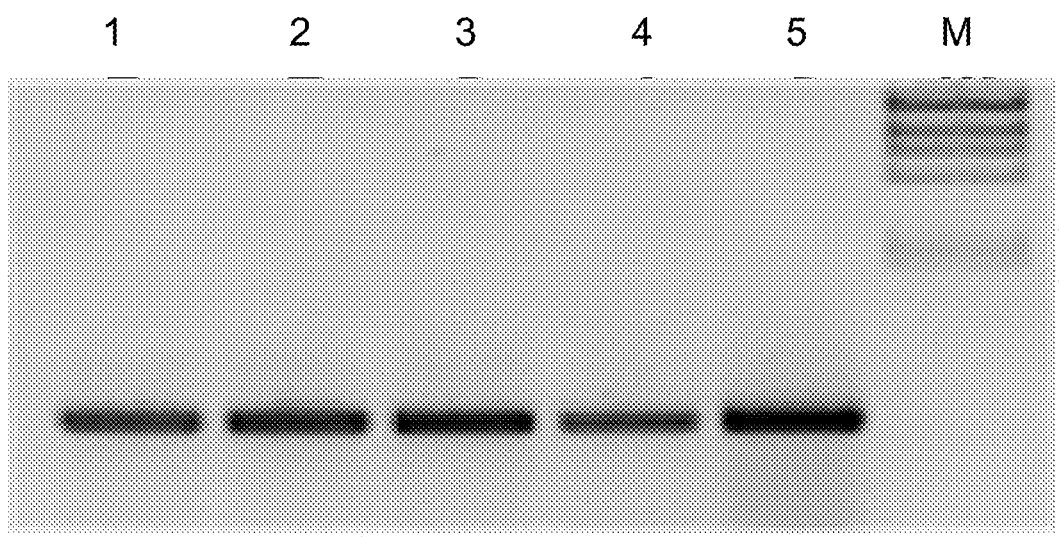
Figure 8A:
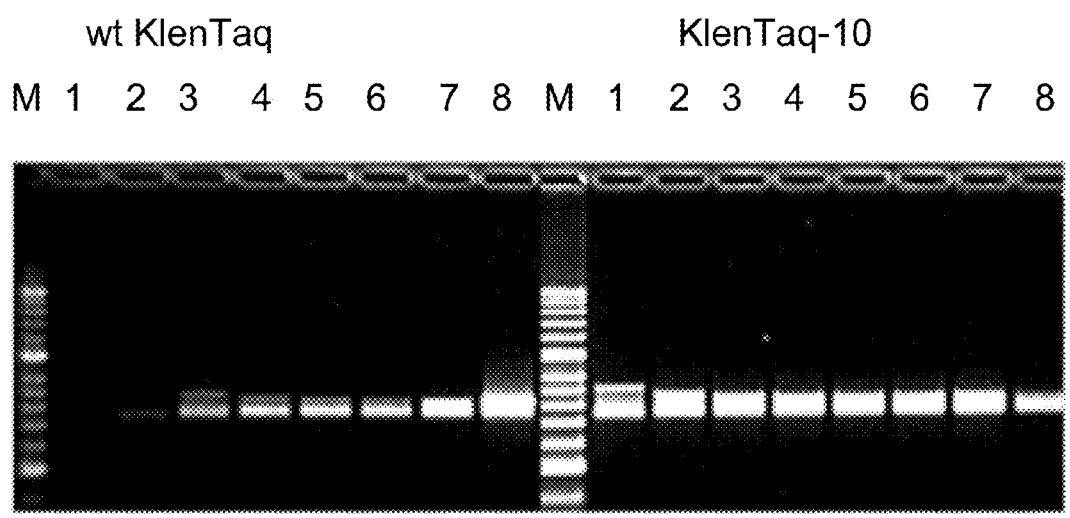
Figure 8B:
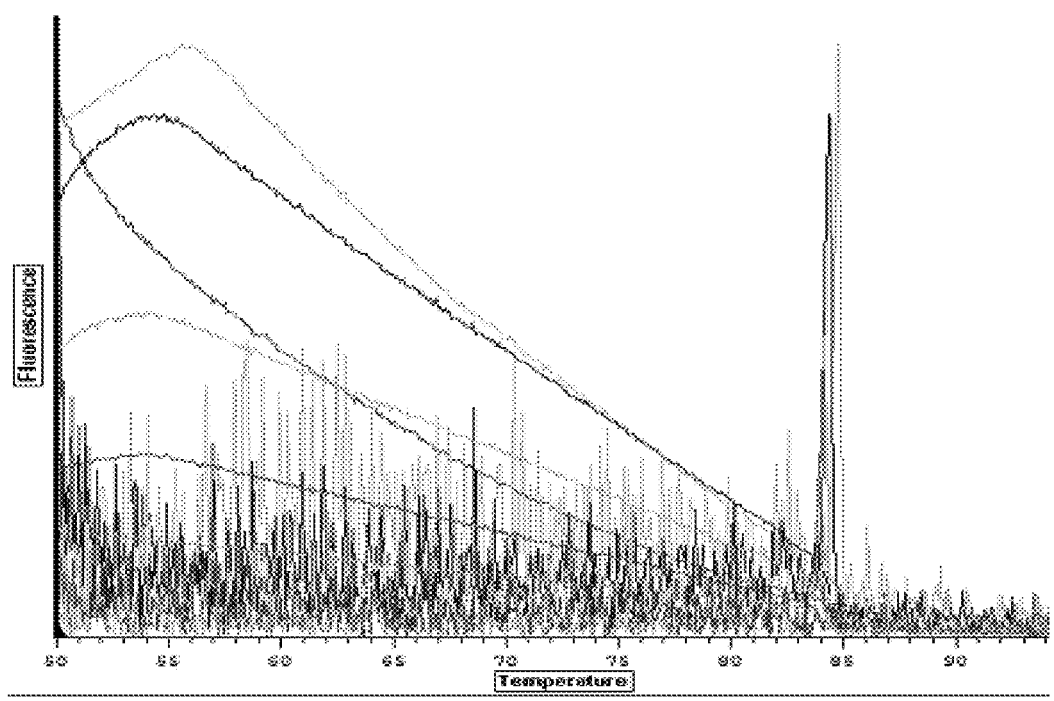
Figure 8C:
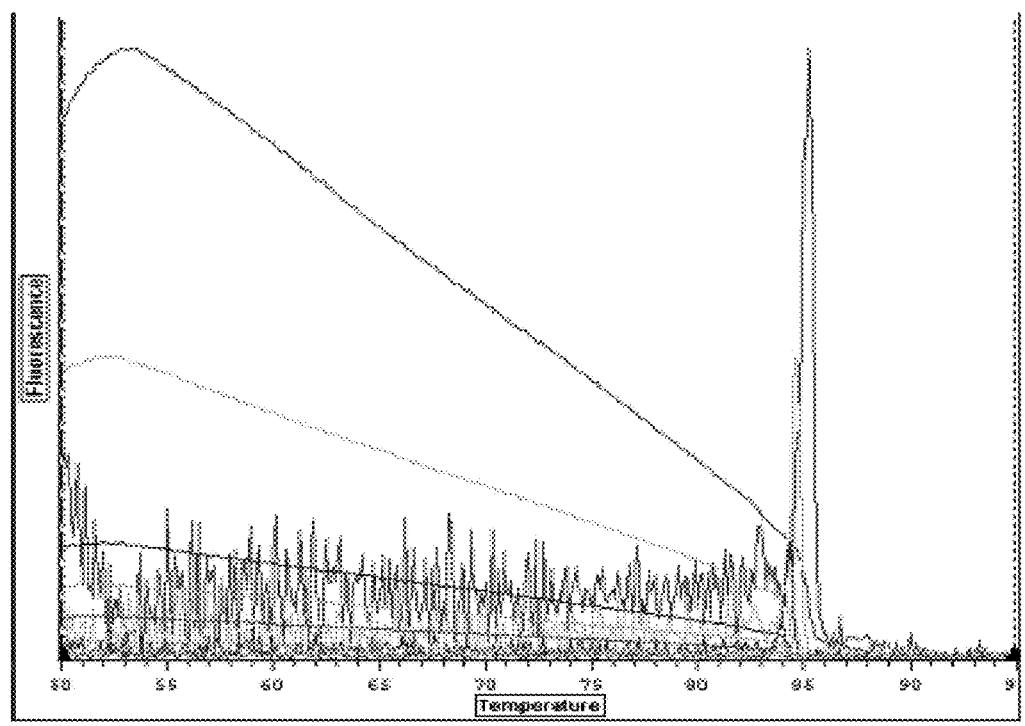
Figure 8D:
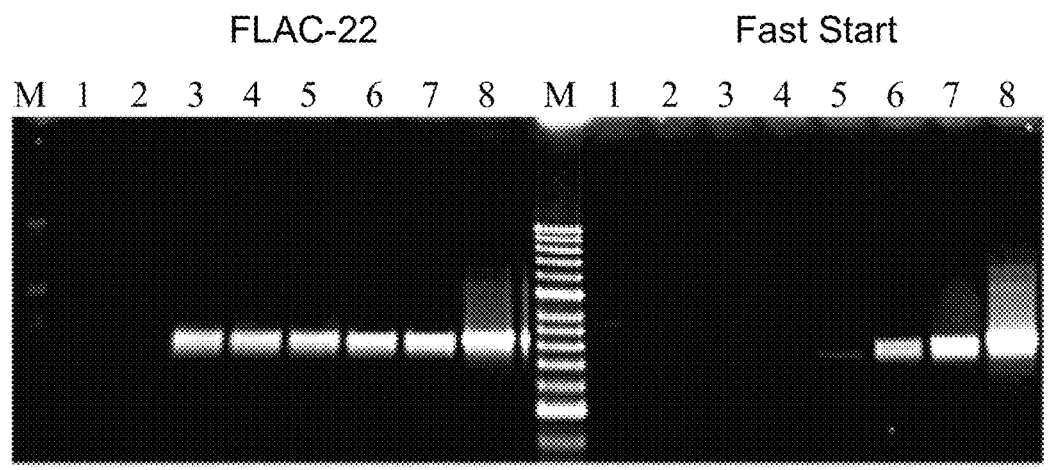
Figure 8E:
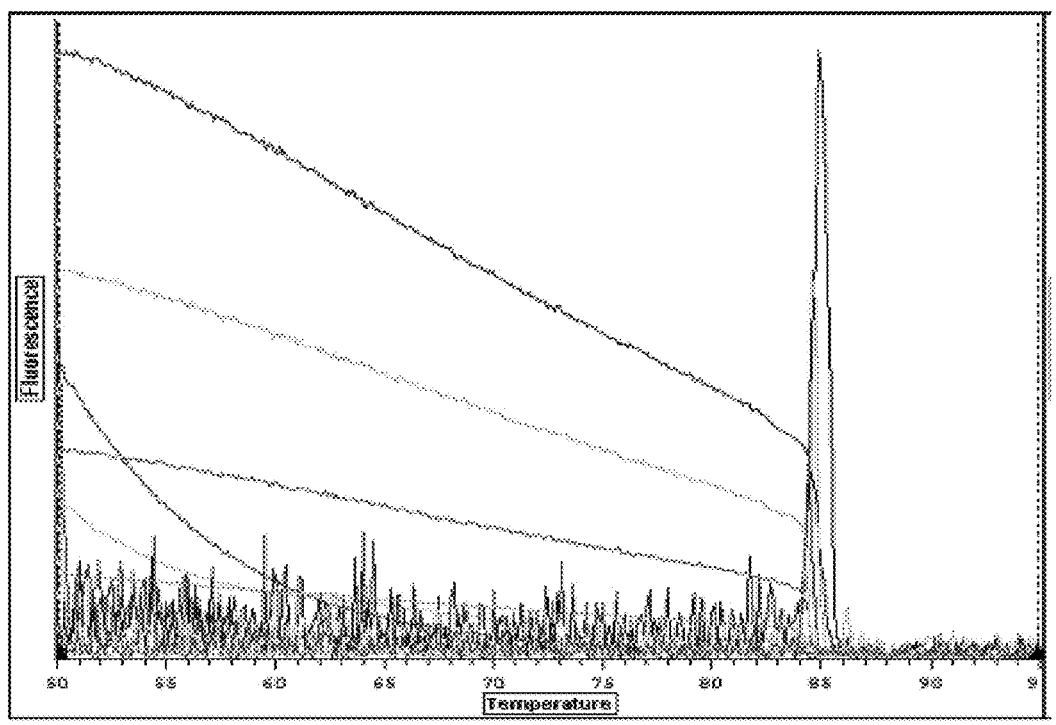
Figure 8F:
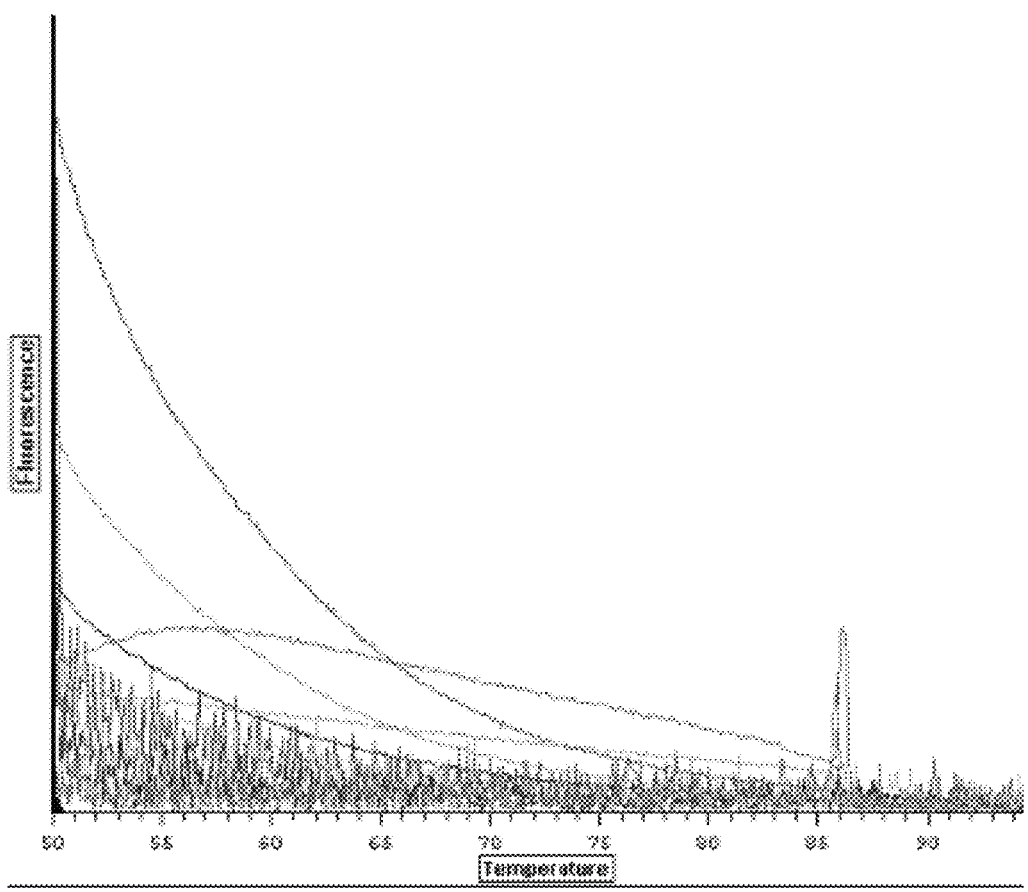

Two commercial Taq enzymes, Fast Start Taq (Roche) and Jump Start Tag (Sigma), and KT-10 mutant enzyme (SEQ ID NO: 1) were used to amplify an endogenous 600 bp target of *Bacillus Cereus* from a crude soil extract. The reactions contained four dilutions of the soil extract: 16%, 8%, 4% and 2% (see e.g., FIG. 7D-E, lanes 1-4, respectively). Reactions in lane 5 were positive controls, containing 5 ng purified *B. cereus* DNA without soil extract. PCR was performed in real-time cycler Opticon-2, and the amplified products were analyzed both by SYBR Green dye fluorescence (top panels) and gel electrophoresis (bottom panels). The pink curves correspond to the control reactions and the yellow, blue, green, and red ones reflect the reactions with increasing soil concentration. This example demonstrates the soil-resistance feature of the mutant Klentaq-10 enzyme, outperforming the two commercial Tags, which require DNA purification from soil prior to PCR.

Example 8

This example demonstrates that in addition to the blood- and SYBR-resistance, the two novel mutant enzymes also possess high tolerance to PCR inhibitors present in soil. A 630 bp CCR5 gene target was amplified from 4 ng of human DNA mixed with crude soil extract and various amounts of SYBR. Klentaq-10 mutant enzyme was compared to it's wild type precursor, and FLAC-22 (SEQ ID NO: 2) was compared to the wild type Fast Start Taq polymerase (Roche). SYBR Green fluorescent dye was titrated to optimize the fluorescent signal for real time detection. PCR was performed in real-time cycler Opticon2, and the amplified products were analyzed both by gel electrophoresis (bottom panels) and SYBR Green dye melting curve profile (top panels).

The soil resistant mutant enzymes showed specific melting curves with very low background signal. In contrast, the wild type Klentaq and Fast Start Taq showed a melting curve at very low SYBR concentration so the signal might get lost in the background in the presence of more soil. The results demonstrate that the two new mutant enzymes can perform easily in real time PCR of crude soil samples containing PCR inhibitors, without requiring pre-PCR DNA purification steps.

Example 9

Single amino acid changes of the wild type Taq Glu708 were implicated in both selected qualities of the mutants, blood and soil-resistance. Functional analysis revealed that the same amino acid substitutions in that position were optimal both for the blood and soil resistance features.

Saturated mutagenesis was performed at codon 708 of Taq to test functionally the full spectrum of all possible substitutions at this critical position. Among all 708 mutant variants, Klentaq-10 (SEQ ID NO: 1) and FLAC-22 (SEQ ID NO: 2) proved superior in all aspects of inhibitors resistance to PCR inhibitors.

The analysis of the 708 changes showed certain specificity for KlenTaq and Taq DNA polymerase. K and L substitutions were efficient in both enzymes (mutants Klentaq10 and 12, and the corresponding FLAC-10 and FLAC-12), while N, Q, I (FLAC-22, 3 and 4) were only functional in Taq, and W substitution was only good in KlenTaq (Klentaq-7).

The two phenotypes were not tightly coupled, as the KlenTaq 7 (E708W) and Klentaq-12 mutants (G708Trp and Glu708Leu) exhibited relatively high resistance to blood but not to soil inhibitors, while another KlenTaq mutant (Klentaq 11, E708R) was predominantly soil resistant. As per the SYBR resistance, next to Klentaq-10 and FLAC-22 (SEQ ID NO: 2) in order of performance were Klentaq-11 (E708R) and Klentaq-12 (E708L).

The importance of residue 708 was confirmed by the fact that two of the possible 20 substitutions, P and C, inactivated both the KlenTaq and Taq enzyme.

Example 10

The following example illustrates real-time RT PCR amplification of crude samples containing blood components utilizing FLAC-22 (SEQ ID NO: 2) and KT-10 (SEQ ID NO: 1).

100 units of MMLV RT were mixed with 1 unit FLAC-22 (SEQ ID NO: 2) and 1 unit KT-10 (SEQ ID NO: 1). The negative controls only contained FLAC-22 (SEQ ID NO: 2) and KT-10 mix and MMLV-RT was omitted. One commercial RT-PCR kit was also included as comparison. Seven pg of influenza virus RNA was spiked in plasma, serum, or whole blood. RT-PCR reactions also contained an enhancer composition containing 0.64 M Trehalose, 0.12 M L-carnitine, 0.4% NP-40 and 10 u heparin per ml serum, plasma, or whole blood (PEC-Plus). One-step RT-PCR reactions (50 µl) containing viral RNA (lane 1) or viral RNA mixed with 8% of plasma (lane 2), serum (lane 3), or blood (lane 4) were performed in PTC-200 Thermal Cycler to amplify a 244 bp influenza virus RNA target. The PCR products were resolved in 1.5% agarose gel.

Figure 9A:
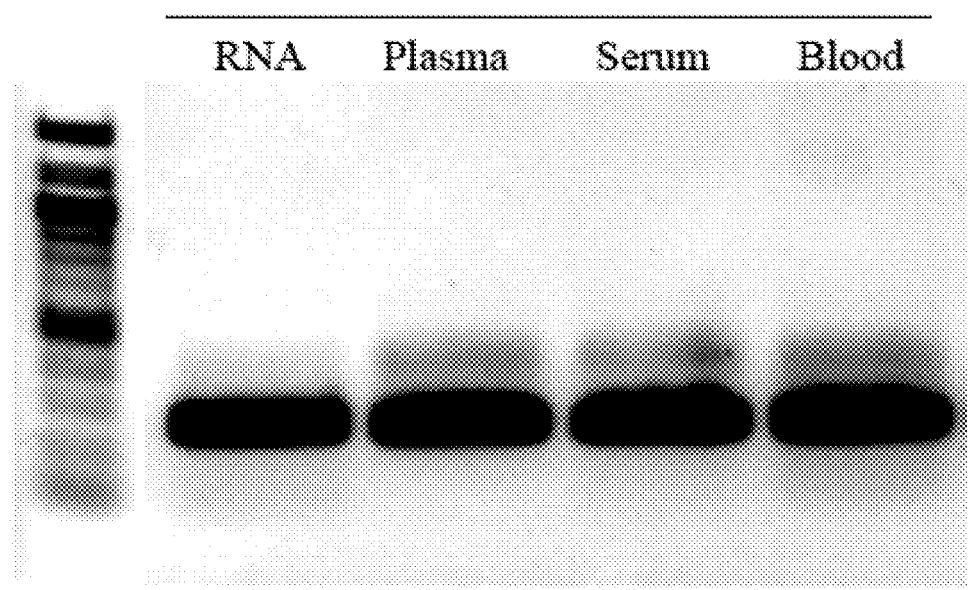
Figure 9B:
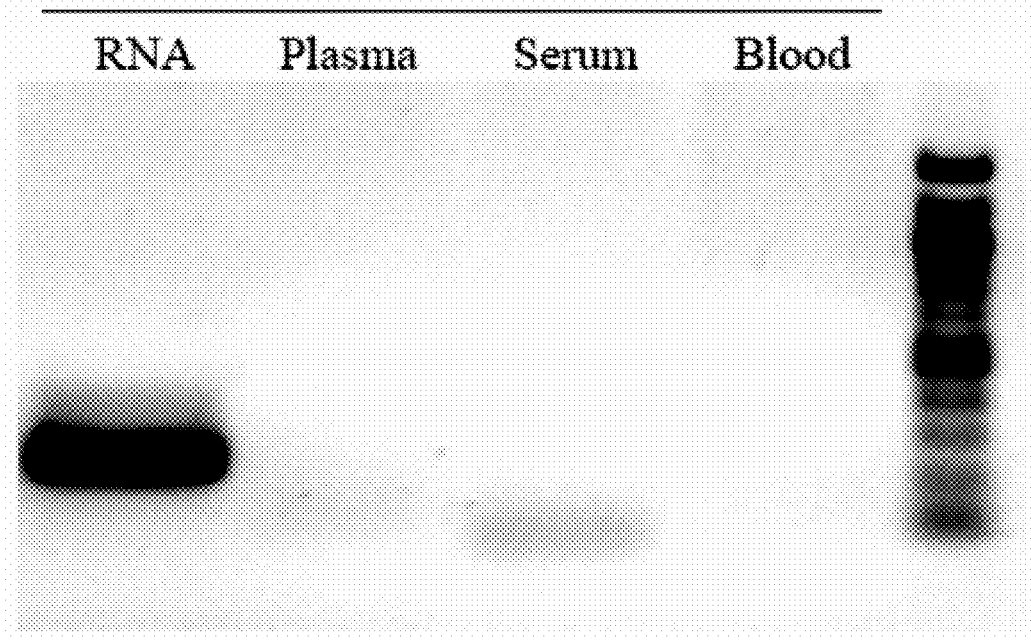
Figure 9C:
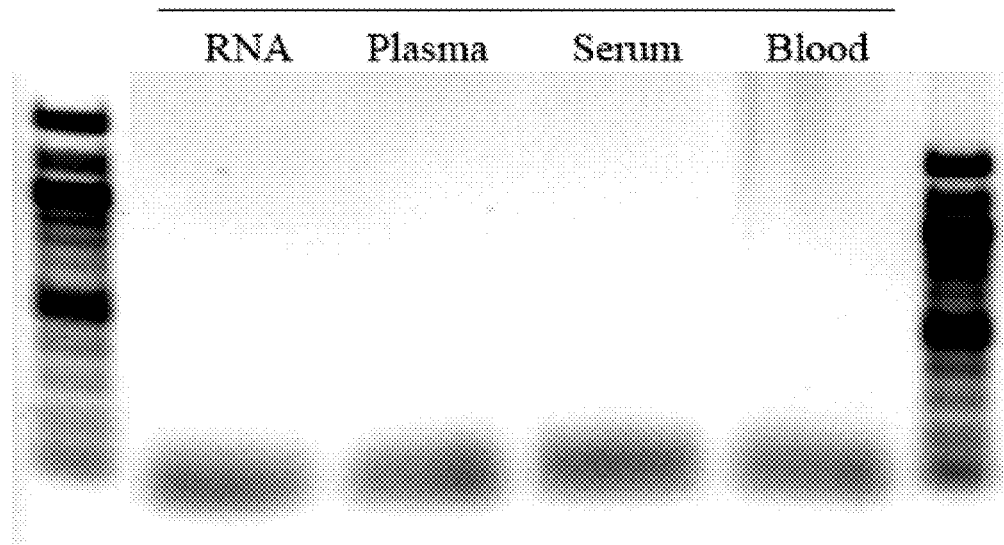
Figure 10A:
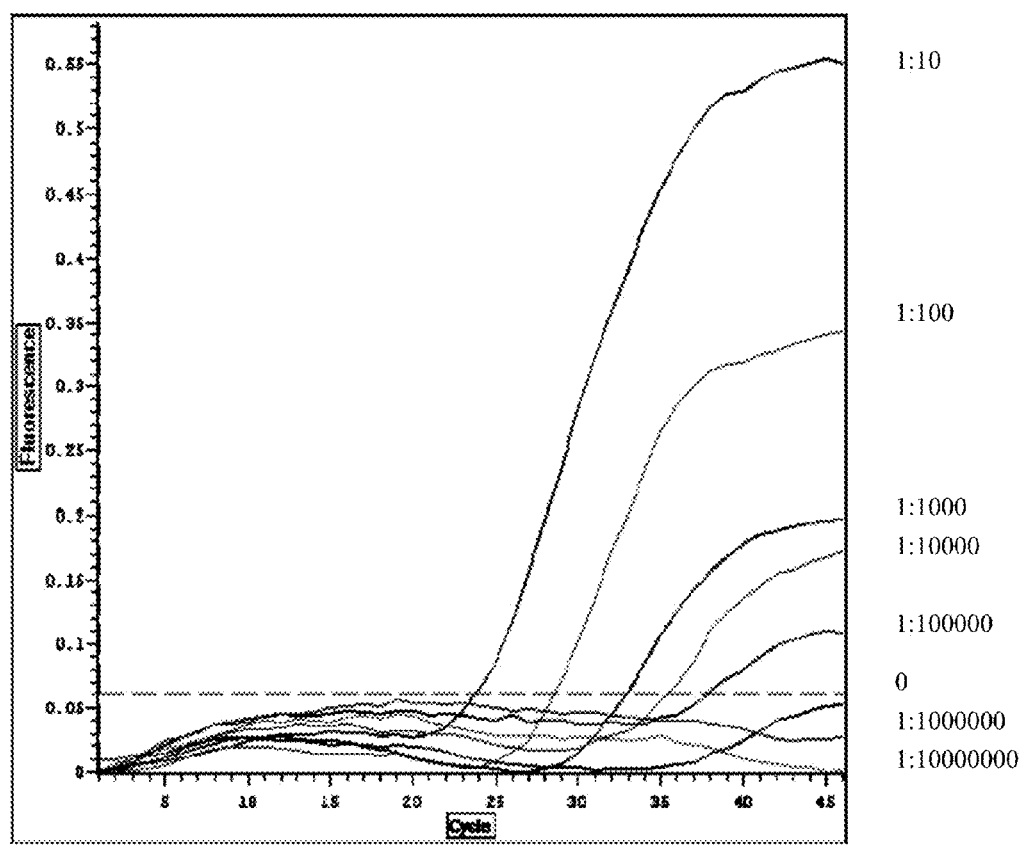
Figure 10B:
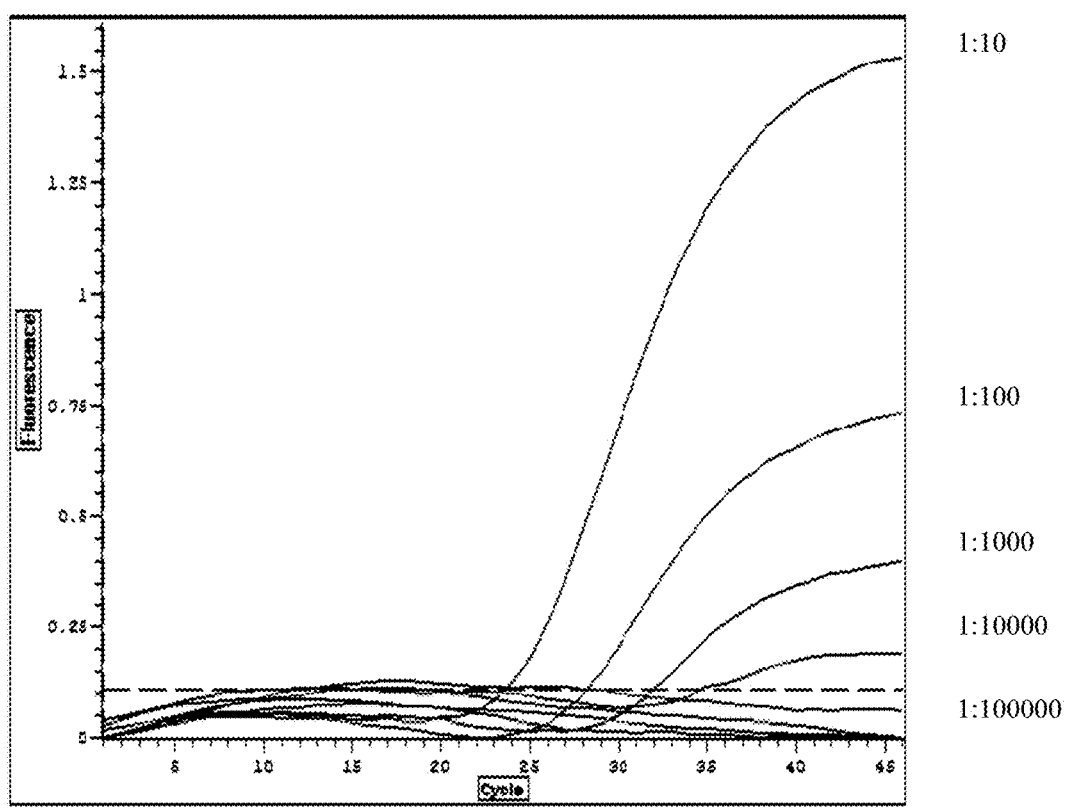

Results showed a 244 bp influenza virus gene was successfully amplified from purified RNA and mimic crude samples containing 8% plasma, serum, and whole blood using an FLAC-22 (SEQ ID NO: 2), KT-10 (SEQ ID NO: 1) and MMLV-RT mixture (see e.g., FIG. 9). Successful amplification of RNA targets was also obtained where FLAC-22 (SEQ ID NO: 2) and KT-10 (SEQ ID NO: 1) were blended with other reverse transcriptase (data not shown).

Results further showed that conventional commercial RT-PCR kits were only able to amplify this target from purified RNA and failed in crude samples due to the presence of potent inhibitors of the Taq DNA polymerase and the reverse transcriptase in such specimens. The negative controls, omitting the reverse transcriptase, produced no specific products. These data show that RT-PCR products were amplifications based on the RNA template and not from cDNA contamination or another source of DNA.

Thus, as demonstrated above, FLAC-22 (SEQ ID NO: 2) and KT-10 (SEQ ID NO: 1) work in RT-PCR for RNA target in crude samples in the presence of reverse transcriptases.

Example 11

The following example illustrates real-time RT PCR TaqMan assay in crude samples containing blood components utilizing FLAC-22 (SEQ ID NO: 2) and KT-10 (SEQ ID NO: 1).

Purified influenza virus RNA was 10-fold diluted 7 times and spiked in human serum. One-step RT-PCR reactions (25 µl) containing different concentrations of RNA and constant concentrations of human serum (5%), were performed with an enzyme mix of 100 units of MMLV RT and 1 unit of FLAC-22 (SEQ ID NO: 2) and 2.5 units of KT-10 (SEQ ID NO: 1). RT-PCR reactions also contained an enhancer composition containing 0.64 M Trehalose, 0.12 M L-carnitine, 0.4% NP-40 and 10 u heparin per ml serum, plasma, or whole blood (PEC-Plus). Parallel reactions with purified viral RNA alone were included as comparison and positive controls. The negative controls contained no RNA template. A 244 bp influenza virus target was amplified in the presence of a 200 µM TaqMan probe. The reactions were performed in an Opticon-2 real-time PCR cycler and the fluorescence signal was detected after the annealing step.

Results showed that the 244 bp influenza virus gene was successfully detected from mimic clinical samples containing 5% human serum, using a combination of FLAC-22 (SEQ ID NO: 2), KT-10 (SEQ ID NO: 1), and MMLV-RT. The fluorescent signal in crude samples was relatively lower than these in purified RNA, however, the sensitivity was not compromised as compared to the results with purified RNA. In addition to serum, these results were confirmed with plasma and whole blood (data not shown). The optimal concentrations of TaqMan was 200-400 µM for 5-20% plasma and serum, and 400-800 µM for 5-10% whole blood.

Thus, as demonstrated above, FLAC-22 (SEQ ID NO: 2) and KT-10 (SEQ ID NO: 1) work in RT-PCR TaqMan assays for RNA target in crude samples in the presence of reverse transcriptases.

The invention claimed is:

1. An isolated polypeptide comprising SEQ ID NO: 2 or a variant thereof having at least 95% sequence identity to SEQ ID NO: 2, wherein,
   position 708 of the variant of SEQ ID NO: 2 is asparagine and
   the variant of SEQ ID NO: 2 has polymerase activity resistant to a polymerase chain reaction (PCR) inhibitor selected from the group consisting of blood, soil, and dye, or a combination thereof.

2. The isolated polypeptide of claim 1, wherein position 626 of the variant of SEQ ID NO: 2 is lysine.

3. The isolated polypeptide of claim 1, wherein position 707 of the variant of SEQ ID NO: 2 is leucine.

4. The isolated polypeptide of claim 1, wherein position 626 of the variant of SEQ ID NO: 2 is lysine and position 707 of the variant of SEQ ID NO: 2 is leucine.

5. The isolated polypeptide of claim 1, wherein the isolated polypeptide has blood resistant polymerase activity.

6. The isolated polypeptide of claim 1, wherein the isolated polypeptide has polymerase activity in a PCR assay mixture comprising at least about 1% up to about 25% of a total volume of whole blood or a blood component.

7. The isolated polypeptide of claim 1, wherein the isolated polypeptide has soil resistant polymerase activity.

8. The isolated polypeptide of claim 1, wherein the isolated polypeptide has polymerase activity in a PCR assay mixture comprising at least about 1% up to about 90% of a total volume of soil or soil extract.

9. The isolated polypeptide of claim 8, wherein the soil or soil extract comprises a humic acid at a concentration up to about 25 ng of humic acid per 50 µL PCR reaction volume.

10. The isolated polypeptide of claim 1, wherein the isolated polypeptide has dye resistant polymerase activity.

11. The isolated polypeptide of claim 1, wherein the isolated polypeptide has polymerase activity in a PCR assay mixture comprising at least one dye present at a concentration of at least about 0.5× up to about 256×, where X is a manufacturer unit for concentration for use in PCR.

12. The isolated polypeptide of claim 11, wherein the at least one dye is a fluorescent dye selected from the group consisting of SYBR Green, Ethidium Bromide, PICO, TOTO, YOYO, and LC Green.

13. The isolated polypeptide of claim 1, wherein the isolated polypeptide comprises SEQ ID NO: 2.

14. The isolated polypeptide of claim 1, wherein the variant of SEQ ID NO: 2 has at least 99% sequence identity to SEQ ID NO: 2.

15. A kit for performing PCR assays, wherein the kit comprises the isolated polypeptide of claim 1.

16. An isolated polypeptide comprising SEQ ID NO: 2 or a variant thereof having at least 85% sequence identity to SEQ ID NO: 2, wherein position 708 of the variant of SEQ ID NO: 2 is asparagine.

17. The isolated polypeptide of claim 16, wherein position 626 of the variant of SEQ ID NO: 2 is lysine.

18. The isolated polypeptide of claim 16, wherein position 707 of the variant of SEQ ID NO: 2 is leucine.

19. The isolated polypeptide of claim 16, wherein position 626 of the variant of SEQ ID NO: 2 is lysine and position 707 of the variant of SEQ ID NO: 2 is leucine.

20. The isolated polypeptide of claim 16, wherein the variant has at least 95% sequence identity to SEQ ID NO: 2.

* * * * *

SEQUENCE LISTING

<160> NUMBER OF SEQ ID NOS: 10

<210> SEQ ID NO 1
<211> LENGTH: 554
<212> TYPE: PRT
<213> ORGANISM: Artificial Sequence
<220> FEATURE:
<223> OTHER INFORMATION: Klentaq-10

<400> SEQUENCE: 1

-continued

```
Met Gly Leu Leu His Glu Phe Gly Leu Leu Glu Ser Pro Lys Ala Leu
1               5                   10                  15

Glu Glu Ala Pro Trp Pro Pro Glu Gly Ala Phe Val Gly Phe Val
            20                  25                  30

Leu Ser Arg Lys Glu Pro Met Trp Ala Asp Leu Leu Ala Leu Ala
        35                  40                  45

Ala Arg Gly Gly Arg Val His Arg Ala Pro Glu Pro Tyr Lys Ala Leu
    50                  55                  60

Arg Asp Leu Lys Glu Ala Arg Gly Leu Leu Ala Lys Asp Leu Ser Val
65                  70                  75                  80

Leu Ala Leu Arg Glu Gly Leu Gly Leu Pro Pro Gly Asp Asp Pro Met
                85                  90                  95

Leu Leu Ala Tyr Leu Leu Asp Pro Ser Asn Thr Thr Pro Glu Gly Val
                100                 105                 110

Ala Arg Arg Tyr Gly Gly Glu Trp Thr Glu Glu Ala Gly Glu Arg Ala
        115                 120                 125

Ala Leu Ser Glu Arg Leu Phe Ala Asn Leu Trp Gly Arg Leu Glu Gly
    130                 135                 140

Glu Glu Arg Leu Leu Trp Leu Tyr Arg Glu Val Glu Arg Pro Leu Ser
145                 150                 155                 160

Ala Val Leu Ala His Met Glu Ala Thr Gly Val Arg Leu Asp Val Ala
                165                 170                 175

Tyr Leu Arg Ala Leu Ser Leu Glu Val Ala Glu Glu Ile Ala Arg Leu
                180                 185                 190

Glu Ala Glu Val Phe Arg Leu Ala Gly His Pro Phe Asn Leu Asn Ser
        195                 200                 205

Arg Asp Gln Leu Glu Arg Val Leu Phe Asp Glu Leu Gly Leu Pro Ala
    210                 215                 220

Ile Gly Lys Thr Glu Lys Thr Gly Lys Arg Ser Thr Ser Ala Ala Val
225                 230                 235                 240

Leu Glu Ala Leu Arg Glu Ala His Pro Ile Val Glu Lys Ile Leu Gln
                245                 250                 255

Tyr Arg Glu Leu Thr Lys Leu Lys Ser Thr Tyr Ile Asp Pro Leu Pro
                260                 265                 270

Asp Leu Ile His Pro Arg Thr Gly Arg Leu His Thr Arg Phe Asn Gln
            275                 280                 285

Thr Ala Thr Ala Thr Gly Arg Leu Ser Ser Ser Asp Pro Asn Leu Gln
290                 295                 300

Asn Ile Pro Val Arg Thr Pro Leu Gly Gln Arg Ile Arg Arg Ala Phe
305                 310                 315                 320

Ile Ala Glu Glu Gly Trp Leu Leu Val Ala Leu Asp Tyr Ser Gln Ile
                325                 330                 335

Glu Leu Arg Val Leu Ala His Leu Ser Gly Asp Lys Asn Leu Ile Arg
                340                 345                 350

Val Phe Gln Glu Gly Arg Asp Ile His Thr Glu Thr Ala Ser Trp Met
                355                 360                 365

Phe Gly Val Pro Arg Glu Ala Val Asp Pro Leu Met Arg Arg Ala Ala
        370                 375                 380

Lys Thr Ile Asn Phe Gly Val Leu Tyr Gly Met Ser Ala His Arg Leu
385                 390                 395                 400

Ser Gln Glu Leu Ala Ile Pro Tyr Glu Glu Ala Gln Ala Phe Ile Glu
                405                 410                 415
```

```
Arg Tyr Phe Gln Ser Phe Pro Lys Val Arg Ala Trp Leu Lys Lys Thr
                420                 425                 430

Leu Glu Glu Gly Arg Arg Gly Tyr Val Glu Thr Leu Phe Gly Arg
            435                 440                 445

Arg Arg Tyr Val Pro Asp Leu Glu Ala Arg Val Lys Ser Val Arg Glu
450                 455                 460

Ala Ala Glu Arg Met Ala Phe Asn Met Pro Val Gln Gly Thr Ala Ala
465                 470                 475                 480

Asp Leu Met Lys Leu Ala Met Val Lys Leu Phe Pro Arg Leu Glu Glu
                485                 490                 495

Met Gly Ala Arg Met Leu Leu Gln Val His Asp Glu Leu Val Leu Glu
            500                 505                 510

Ala Pro Lys Glu Arg Ala Glu Ala Val Ala Arg Leu Ala Lys Glu Val
        515                 520                 525

Met Glu Gly Val Tyr Pro Leu Ala Val Pro Leu Glu Val Glu Val Gly
            530                 535                 540

Ile Gly Glu Asp Trp Leu Ser Ala Lys Glu
545                 550

<210> SEQ ID NO 2
<211> LENGTH: 832
<212> TYPE: PRT
<213> ORGANISM: Artificial Sequence
<220> FEATURE:
<223> OTHER INFORMATION: FLAC-22

<400> SEQUENCE: 2

Met Arg Gly Met Leu Pro Leu Phe Glu Pro Lys Gly Arg Val Leu Leu
1               5                   10                  15

Val Asp Gly His His Leu Ala Tyr Arg Thr Phe His Ala Leu Lys Gly
            20                  25                  30

Leu Thr Thr Ser Arg Gly Glu Pro Val Gln Ala Val Tyr Gly Phe Ala
        35                  40                  45

Lys Ser Leu Leu Lys Ala Leu Lys Glu Asp Gly Asp Ala Val Ile Val
    50                  55                  60

Val Phe Asp Ala Lys Ala Pro Ser Phe Arg His Glu Ala Tyr Gly Gly
65                  70                  75                  80

Tyr Lys Ala Gly Arg Ala Pro Thr Pro Glu Asp Phe Pro Arg Gln Leu
                85                  90                  95

Ala Leu Ile Lys Glu Leu Val Asp Leu Leu Gly Leu Ala Arg Leu Glu
            100                 105                 110

Val Pro Gly Tyr Glu Ala Asp Asp Val Leu Ala Ser Leu Ala Lys Lys
        115                 120                 125

Ala Glu Lys Glu Gly Tyr Glu Val Arg Ile Leu Thr Ala Asp Lys Asp
    130                 135                 140

Leu Tyr Gln Leu Leu Ser Asp Arg Ile His Val Leu His Pro Glu Gly
145                 150                 155                 160

Tyr Leu Ile Thr Pro Ala Trp Leu Trp Glu Lys Tyr Gly Leu Arg Pro
                165                 170                 175

Asp Gln Trp Ala Asp Tyr Arg Ala Leu Thr Gly Asp Glu Ser Asp Asn
            180                 185                 190

Leu Pro Gly Val Lys Gly Ile Gly Glu Lys Thr Ala Arg Lys Leu Leu
        195                 200                 205

Glu Glu Trp Gly Ser Leu Glu Ala Leu Leu Lys Asn Leu Asp Arg Leu
    210                 215                 220
```

-continued

```
Lys Pro Ala Ile Arg Glu Lys Ile Leu Ala His Met Asp Asp Leu Lys
225                 230                 235                 240

Leu Ser Trp Asp Leu Ala Lys Val Arg Thr Asp Leu Pro Leu Glu Val
            245                 250                 255

Asp Phe Ala Lys Arg Arg Glu Pro Asp Arg Glu Arg Leu Arg Ala Phe
        260                 265                 270

Leu Glu Arg Leu Glu Phe Gly Ser Leu Leu His Glu Phe Gly Leu Leu
    275                 280                 285

Glu Ser Pro Lys Ala Leu Glu Ala Pro Trp Pro Pro Glu Gly
290                 295                 300

Ala Phe Val Gly Phe Val Leu Ser Arg Lys Glu Pro Met Trp Ala Asp
305                 310                 315                 320

Leu Leu Ala Leu Ala Ala Arg Gly Gly Arg Val His Arg Ala Pro
            325                 330                 335

Glu Pro Tyr Lys Ala Leu Arg Asp Leu Lys Glu Ala Arg Gly Leu Leu
        340                 345                 350

Ala Lys Asp Leu Ser Val Leu Ala Leu Arg Glu Gly Leu Gly Leu Pro
    355                 360                 365

Pro Gly Asp Asp Pro Met Leu Leu Ala Tyr Leu Leu Asp Pro Ser Asn
370                 375                 380

Thr Thr Pro Glu Gly Val Ala Arg Arg Tyr Gly Gly Glu Trp Thr Glu
385                 390                 395                 400

Glu Ala Gly Glu Arg Ala Ala Leu Ser Glu Arg Leu Phe Ala Asn Leu
            405                 410                 415

Trp Gly Arg Leu Glu Gly Glu Glu Arg Leu Leu Trp Leu Tyr Arg Glu
        420                 425                 430

Val Glu Arg Pro Leu Ser Ala Val Leu Ala His Met Glu Ala Thr Gly
    435                 440                 445

Val Arg Leu Asp Val Ala Tyr Leu Arg Ala Leu Ser Leu Glu Val Ala
450                 455                 460

Glu Glu Ile Ala Arg Leu Glu Ala Glu Val Phe Arg Leu Ala Gly His
465                 470                 475                 480

Pro Phe Asn Leu Asn Ser Arg Asp Gln Leu Glu Arg Val Leu Phe Asp
            485                 490                 495

Glu Leu Gly Leu Pro Ala Ile Gly Lys Thr Glu Lys Thr Gly Lys Arg
        500                 505                 510

Ser Thr Ser Ala Ala Val Leu Glu Ala Leu Arg Glu Ala His Pro Ile
    515                 520                 525

Val Glu Lys Ile Leu Gln Tyr Arg Glu Leu Thr Lys Leu Lys Ser Thr
530                 535                 540

Tyr Ile Asp Pro Leu Pro Asp Leu Ile His Pro Arg Thr Gly Arg Leu
545                 550                 555                 560

His Thr Arg Phe Asn Gln Thr Ala Thr Ala Thr Gly Arg Leu Ser Ser
            565                 570                 575

Ser Asp Pro Asn Leu Gln Asn Ile Pro Val Arg Thr Pro Leu Gly Gln
        580                 585                 590

Arg Ile Arg Arg Ala Phe Ile Ala Glu Glu Gly Trp Leu Leu Val Ala
    595                 600                 605

Leu Asp Tyr Ser Gln Ile Glu Leu Arg Val Leu Ala His Leu Ser Gly
610                 615                 620

Asp Lys Asn Leu Ile Arg Val Phe Gln Glu Gly Arg Asp Ile His Thr
625                 630                 635                 640

Glu Thr Ala Ser Trp Met Phe Gly Val Pro Arg Glu Ala Val Asp Pro
```

```
                        645                 650                 655
Leu Met Arg Arg Ala Ala Lys Thr Ile Asn Phe Gly Val Leu Tyr Gly
            660                 665                 670

Met Ser Ala His Arg Leu Ser Gln Glu Leu Ala Ile Pro Tyr Glu Glu
        675                 680                 685

Ala Gln Ala Phe Ile Glu Arg Tyr Phe Gln Ser Phe Pro Lys Val Arg
        690                 695                 700

Ala Trp Leu Asn Lys Thr Leu Glu Glu Gly Arg Arg Arg Gly Tyr Val
705                 710                 715                 720

Glu Thr Leu Phe Gly Arg Arg Tyr Val Pro Asp Leu Glu Ala Arg
                725                 730                 735

Val Lys Ser Val Arg Glu Ala Ala Glu Arg Met Ala Phe Asn Met Pro
            740                 745                 750

Val Gln Gly Thr Ala Ala Asp Leu Met Lys Leu Ala Met Val Lys Leu
        755                 760                 765

Phe Pro Arg Leu Glu Glu Met Gly Ala Arg Met Leu Leu Gln Val His
770                 775                 780

Asp Glu Leu Val Leu Glu Ala Pro Lys Glu Arg Ala Glu Ala Val Ala
785                 790                 795                 800

Arg Leu Ala Lys Glu Val Met Glu Gly Val Tyr Pro Leu Ala Val Pro
                805                 810                 815

Leu Glu Val Glu Val Gly Ile Gly Glu Asp Trp Leu Ser Ala Lys Glu
            820                 825                 830

<210> SEQ ID NO 3
<211> LENGTH: 554
<212> TYPE: PRT
<213> ORGANISM: Artificial Sequence
<220> FEATURE:
<223> OTHER INFORMATION: Klentaq-1

<400> SEQUENCE: 3

Met Gly Leu Leu His Glu Phe Gly Leu Leu Glu Ser Pro Lys Ala Leu
1               5                   10                  15

Glu Glu Ala Pro Trp Pro Pro Pro Glu Gly Ala Phe Val Gly Phe Val
            20                  25                  30

Leu Ser Arg Lys Glu Pro Met Trp Ala Asp Leu Leu Ala Leu Ala Ala
        35                  40                  45

Ala Arg Gly Gly Arg Val His Arg Ala Pro Glu Pro Tyr Lys Ala Leu
    50                  55                  60

Arg Asp Leu Lys Glu Ala Arg Gly Leu Leu Ala Lys Asp Leu Ser Val
65                  70                  75                  80

Leu Ala Leu Arg Glu Gly Leu Gly Leu Pro Pro Gly Asp Asp Pro Met
                85                  90                  95

Leu Leu Ala Tyr Leu Leu Asp Pro Ser Asn Thr Thr Pro Glu Gly Val
            100                 105                 110

Ala Arg Arg Tyr Gly Gly Glu Trp Thr Glu Glu Ala Gly Glu Arg Ala
        115                 120                 125

Ala Leu Ser Glu Arg Leu Phe Ala Asn Leu Trp Gly Arg Leu Glu Gly
    130                 135                 140

Glu Glu Arg Leu Leu Trp Leu Tyr Arg Glu Val Glu Arg Pro Leu Ser
145                 150                 155                 160

Ala Val Leu Ala His Met Glu Ala Thr Gly Val Arg Leu Asp Val Ala
                165                 170                 175

Tyr Leu Arg Ala Leu Ser Leu Glu Val Ala Glu Glu Ile Ala Arg Leu
```

```
                180                 185                 190
        Glu Ala Glu Val Phe Arg Leu Ala Gly His Pro Phe Asn Leu Asn Ser
            195                 200                 205

Arg Asp Gln Leu Glu Arg Val Leu Phe Asp Glu Leu Gly Leu Pro Ala
        210                 215                 220

Ile Gly Lys Thr Glu Lys Thr Gly Lys Arg Ser Thr Ser Ala Ala Val
        225                 230                 235                 240

Leu Glu Ala Leu Arg Glu Ala His Pro Ile Val Glu Lys Ile Leu Gln
                        245                 250                 255

Tyr Arg Glu Leu Thr Lys Leu Lys Ser Thr Tyr Ile Asp Pro Leu Pro
                        260                 265                 270

Asp Leu Ile His Pro Arg Thr Gly Arg Leu His Thr Arg Phe Asn Gln
                        275                 280                 285

Thr Ala Thr Ala Thr Gly Arg Leu Ser Ser Ser Asp Pro Asn Leu Gln
                        290                 295                 300

Asn Ile Pro Val Arg Thr Pro Leu Gly Gln Arg Ile Arg Arg Ala Phe
        305                 310                 315                 320

Ile Ala Glu Glu Gly Trp Leu Leu Val Ala Leu Asp Tyr Ser Gln Ile
                        325                 330                 335

Glu Leu Arg Val Leu Ala His Leu Ser Gly Asp Glu Asn Leu Ile Arg
                        340                 345                 350

Val Phe Gln Glu Gly Arg Asp Ile His Thr Glu Thr Ala Ser Trp Met
                        355                 360                 365

Phe Gly Val Pro Arg Glu Ala Val Asp Pro Leu Met Arg Arg Ala Ala
                        370                 375                 380

Lys Thr Ile Asn Phe Gly Val Leu Tyr Gly Met Ser Ala His Arg Leu
        385                 390                 395                 400

Ser Gln Glu Leu Ala Ile Pro Tyr Glu Glu Ala Gln Ala Phe Ile Glu
                        405                 410                 415

Arg Tyr Phe Gln Ser Phe Pro Lys Val Arg Ala Trp Ile Glu Lys Thr
                        420                 425                 430

Leu Glu Glu Gly Arg Arg Gly Tyr Val Glu Thr Leu Phe Gly Arg
                        435                 440                 445

Arg Arg Tyr Val Pro Asp Leu Glu Ala Arg Val Lys Ser Val Arg Glu
                        450                 455                 460

Ala Ala Glu Arg Met Ala Phe Asn Met Pro Val Gln Gly Thr Ala Ala
        465                 470                 475                 480

Asp Leu Met Lys Leu Ala Met Val Lys Leu Phe Pro Arg Leu Glu Glu
                        485                 490                 495

Met Gly Ala Arg Met Leu Leu Gln Val His Asp Glu Leu Val Leu Glu
                        500                 505                 510

Ala Pro Lys Glu Arg Ala Glu Ala Val Ala Arg Leu Ala Lys Glu Val
                        515                 520                 525

Met Glu Gly Val Tyr Pro Leu Ala Val Pro Leu Glu Val Glu Val Gly
                        530                 535                 540

Ile Gly Glu Asp Trp Leu Ser Ala Lys Glu
        545                 550

<210> SEQ ID NO 4
<211> LENGTH: 832
<212> TYPE: PRT
<213> ORGANISM: Thermus aquaticus

<400> SEQUENCE: 4
```

```
Met Arg Gly Met Leu Pro Leu Phe Glu Pro Lys Gly Arg Val Leu Leu
1               5                   10                  15

Val Asp Gly His His Leu Ala Tyr Arg Thr Phe His Ala Leu Lys Gly
            20                  25                  30

Leu Thr Thr Ser Arg Gly Glu Pro Val Gln Ala Val Tyr Gly Phe Ala
        35                  40                  45

Lys Ser Leu Leu Lys Ala Leu Lys Glu Asp Gly Asp Ala Val Ile Val
    50                  55                  60

Val Phe Asp Ala Lys Ala Pro Ser Phe Arg His Glu Ala Tyr Gly Gly
65                  70                  75                  80

Tyr Lys Ala Gly Arg Ala Pro Thr Pro Glu Asp Phe Pro Arg Gln Leu
                85                  90                  95

Ala Leu Ile Lys Glu Leu Val Asp Leu Leu Gly Leu Ala Arg Leu Glu
            100                 105                 110

Val Pro Gly Tyr Glu Ala Asp Asp Val Leu Ala Ser Leu Ala Lys Lys
        115                 120                 125

Ala Glu Lys Glu Gly Tyr Glu Val Arg Ile Leu Thr Ala Asp Lys Asp
    130                 135                 140

Leu Tyr Gln Leu Leu Ser Asp Arg Ile His Val Leu His Pro Glu Gly
145                 150                 155                 160

Tyr Leu Ile Thr Pro Ala Trp Leu Trp Glu Lys Tyr Gly Leu Arg Pro
                165                 170                 175

Asp Gln Trp Ala Asp Tyr Arg Ala Leu Thr Gly Asp Glu Ser Asp Asn
            180                 185                 190

Leu Pro Gly Val Lys Gly Ile Gly Glu Lys Thr Ala Arg Lys Leu Leu
        195                 200                 205

Glu Glu Trp Gly Ser Leu Glu Ala Leu Lys Asn Leu Asp Arg Leu
    210                 215                 220

Lys Pro Ala Ile Arg Glu Lys Ile Leu Ala His Met Asp Asp Leu Lys
225                 230                 235                 240

Leu Ser Trp Asp Leu Ala Lys Val Arg Thr Asp Leu Pro Leu Glu Val
                245                 250                 255

Asp Phe Ala Lys Arg Arg Glu Pro Asp Arg Glu Arg Leu Arg Ala Phe
            260                 265                 270

Leu Glu Arg Leu Glu Phe Gly Ser Leu Leu His Glu Phe Gly Leu Leu
        275                 280                 285

Glu Ser Pro Lys Ala Leu Glu Glu Ala Pro Trp Pro Pro Pro Glu Gly
    290                 295                 300

Ala Phe Val Gly Phe Val Leu Ser Arg Lys Glu Pro Met Trp Ala Asp
305                 310                 315                 320

Leu Leu Ala Leu Ala Ala Ala Arg Gly Gly Arg Val His Arg Ala Pro
                325                 330                 335

Glu Pro Tyr Lys Ala Leu Arg Asp Leu Lys Glu Ala Arg Gly Leu Leu
            340                 345                 350

Ala Lys Asp Leu Ser Val Leu Ala Leu Arg Glu Gly Leu Gly Leu Pro
        355                 360                 365

Pro Gly Asp Asp Pro Met Leu Leu Ala Tyr Leu Leu Asp Pro Ser Asn
370                 375                 380

Thr Thr Pro Glu Gly Val Ala Arg Arg Tyr Gly Gly Glu Trp Thr Glu
385                 390                 395                 400

Glu Ala Gly Glu Arg Ala Ala Leu Ser Glu Arg Leu Phe Ala Asn Leu
                405                 410                 415

Trp Gly Arg Leu Glu Gly Glu Glu Arg Leu Leu Trp Leu Tyr Arg Glu
```

```
                420             425             430
Val Glu Arg Pro Leu Ser Ala Val Leu Ala His Met Glu Ala Thr Gly
            435             440             445

Val Arg Leu Asp Val Ala Tyr Leu Arg Ala Leu Ser Leu Glu Val Ala
450             455             460

Glu Glu Ile Ala Arg Leu Glu Ala Glu Val Phe Arg Leu Ala Gly His
465             470             475             480

Pro Phe Asn Leu Asn Ser Arg Asp Gln Leu Glu Arg Val Leu Phe Asp
                485             490             495

Glu Leu Gly Leu Pro Ala Ile Gly Lys Thr Glu Lys Thr Gly Lys Arg
            500             505             510

Ser Thr Ser Ala Ala Val Leu Glu Ala Leu Arg Glu Ala His Pro Ile
            515             520             525

Val Glu Lys Ile Leu Gln Tyr Arg Glu Leu Thr Lys Leu Lys Ser Thr
            530             535             540

Tyr Ile Asp Pro Leu Pro Asp Leu Ile His Pro Arg Thr Gly Arg Leu
545             550             555             560

His Thr Arg Phe Asn Gln Thr Ala Thr Ala Thr Gly Arg Leu Ser Ser
                565             570             575

Ser Asp Pro Asn Leu Gln Asn Ile Pro Val Arg Thr Pro Leu Gly Gln
            580             585             590

Arg Ile Arg Arg Ala Phe Ile Ala Glu Glu Gly Trp Leu Leu Val Ala
            595             600             605

Leu Asp Tyr Ser Gln Ile Glu Leu Arg Val Leu Ala His Leu Ser Gly
            610             615             620

Asp Glu Asn Leu Ile Arg Val Phe Gln Glu Gly Arg Asp Ile His Thr
625             630             635             640

Glu Thr Ala Ser Trp Met Phe Gly Val Pro Arg Glu Ala Val Asp Pro
                645             650             655

Leu Met Arg Arg Ala Ala Lys Thr Ile Asn Phe Gly Val Leu Tyr Gly
            660             665             670

Met Ser Ala His Arg Leu Ser Gln Glu Leu Ala Ile Pro Tyr Glu Glu
            675             680             685

Ala Gln Ala Phe Ile Glu Arg Tyr Phe Gln Ser Phe Pro Lys Val Arg
            690             695             700

Ala Trp Ile Glu Lys Thr Leu Glu Glu Gly Arg Arg Arg Gly Tyr Val
705             710             715             720

Glu Thr Leu Phe Gly Arg Arg Arg Tyr Val Pro Asp Leu Glu Ala Arg
                725             730             735

Val Lys Ser Val Arg Glu Ala Ala Glu Arg Met Ala Phe Asn Met Pro
            740             745             750

Val Gln Gly Thr Ala Ala Asp Leu Met Lys Leu Ala Met Val Lys Leu
            755             760             765

Phe Pro Arg Leu Glu Glu Met Gly Ala Arg Met Leu Leu Gln Val His
            770             775             780

Asp Glu Leu Val Leu Glu Ala Pro Lys Glu Arg Ala Glu Ala Val Ala
785             790             795             800

Arg Leu Ala Lys Glu Val Met Glu Gly Val Tyr Pro Leu Ala Val Pro
                805             810             815

Leu Glu Val Glu Val Gly Ile Gly Glu Asp Trp Leu Ser Ala Lys Glu
            820             825             830

<210> SEQ ID NO 5
```

```
<211> LENGTH: 19
<212> TYPE: DNA
<213> ORGANISM: Artificial Sequence
<220> FEATURE:
<223> OTHER INFORMATION: primer

<400> SEQUENCE: 5
agggtcattg gaaactggg                                                    19

<210> SEQ ID NO 6
<211> LENGTH: 21
<212> TYPE: DNA
<213> ORGANISM: Artificial Sequence
<220> FEATURE:
<223> OTHER INFORMATION: primer

<400> SEQUENCE: 6
cgtgttgtag cccaggtcat a                                                 21

<210> SEQ ID NO 7
<211> LENGTH: 23
<212> TYPE: DNA
<213> ORGANISM: Artificial Sequence
<220> FEATURE:
<223> OTHER INFORMATION: primer

<400> SEQUENCE: 7
ggatgcaagc gttatccgga atg                                               23

<210> SEQ ID NO 8
<211> LENGTH: 23
<212> TYPE: DNA
<213> ORGANISM: Artificial Sequence
<220> FEATURE:
<223> OTHER INFORMATION: primer

<400> SEQUENCE: 8
cattcttgcg aacgtactcc cca                                               23

<210> SEQ ID NO 9
<211> LENGTH: 25
<212> TYPE: DNA
<213> ORGANISM: Artificial Sequence
<220> FEATURE:
<223> OTHER INFORMATION: primer

<400> SEQUENCE: 9
gggcggcgac ctcgcgggtt ttcgc                                             25

<210> SEQ ID NO 10
<211> LENGTH: 25
<212> TYPE: DNA
<213> ORGANISM: Artificial Sequence
<220> FEATURE:
<223> OTHER INFORMATION: primer

<400> SEQUENCE: 10
ctgaatggta cggatactcg caccg                                             25
```